United States Patent
Schudok et al.

(10) Patent No.: US 6,706,715 B2
(45) Date of Patent: Mar. 16, 2004

(54) UREA DERIVATIVES WITH ANTIPROTEOLYTIC ACTIVITY

(75) Inventors: Manfred Schudok, Eppstein/Ts (DE); Otmar Klingler, Rodgau (DE); Hans-Peter Nestler, Kelkheim (DE); Hans Matter, Langenselbold (DE); Herman Schreuder, Hofheim-Lorsbach (DE); Hauke Szillat, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/183,848

(22) Filed: Jun. 26, 2002

(65) Prior Publication Data

US 2003/0176439 A1 Sep. 18, 2003

(30) Foreign Application Priority Data

Jun. 26, 2001 (EP) .............................. 01115353

(51) Int. Cl.$^7$ ................ A61K 31/4425; A61K 31/4965; C07D 413/04; C07D 498/02; C07C 233/01
(52) U.S. Cl. .............................. 514/252.05; 514/238.2; 514/352; 514/359; 514/447; 514/452; 514/471; 544/236; 544/238; 546/115; 546/269.1; 546/332; 564/191
(58) Field of Search ................ 546/332, 115, 546/269.1; 564/191; 514/238.2, 352, 359, 447, 452, 471, 252.05, 303, 340; 544/236, 238

(56) References Cited

FOREIGN PATENT DOCUMENTS

| EP | 0987274 | 3/2000 |
|---|---|---|
| WO | WO92/06711 | 4/1992 |
| WO | WO96/12800 | 5/1996 |
| WO | WO97/47651 | 12/1997 |

OTHER PUBLICATIONS

Cheng, Yung–Chi et al., Relationship Between the Inhibition Constant (KI) and the Concentration of Inhibitor which causes 50 Per Cent Inhibition (I50) of an Enzymatic Reaction, Biochem. Pharmacol., vol. 22, pp.3099–3108, 1973.

Harker, Laurence A. et al., Antithrombotic Benefits and Hemorrhagic Risks of Direct Thrombin Antagonists, Thrombosis and Haemostasis, vol. 74(1), pp. 464–472, 1995.

Harker, Laurence A. et al., Antithrombotic and Antilesion Benefits without Hemorrhagic Risks by Inhibiting Tissue Factor Pathway, Haemostasis, vol. 26 (Suppl 1), pp. 76–82, 1996.

Ostrem, James A. et al., Discovery of a Novel, Potent, and Specific Family of Factor Xa Inhibitors via Combinatorial Chemistry, Biochemistry, vol. 37, pp. 1053–1059, 1998.

Segel, Irwin H., Behavior and Analysis of Rapid Equiibrium and Steady–State Enzyme Systems, Enzyme Kinetics, John Wiley & Sons, pp. 100–125, 1975.

Primary Examiner—Taofiq Solola
(74) Attorney, Agent, or Firm—Jiang Lin

(57) ABSTRACT

The present invention relates to compounds of the formula I, $$D_2-N \quad X_1=X_2 \quad \overset{H}{N}\underset{X_3}{\overset{}{\diagup}}\overset{A}{\diagdown}\overset{R^1}{\diagup}$$
$$D_1-\underset{H}{N} \quad \quad R^4 \quad R^5 \quad \quad B\overset{}{\diagdown}R^2$$

(I)

in which $R^1$, $R^2$, $R^4$, $R^5$, $D_1$, $D_2$, $X_1$, $X_2$, $X_3$, A and B have the meanings indicated in the claims. The compounds of the formula I are valuable pharmacologically active compounds. They exhibit a strong antithrombotic effect and are suitable, for example, for the therapy and prophylaxis of thromboembolic diseases and restenoses. They are reversible inhibitors of the blood clotting enzyme factor VIIa and can in general be applied in conditions in which an undesired activity of factor VIIa is present or for the cure or prevention of which an inhibition of factor VIIa is intended. The invention furthermore relates to processes for the preparation of compounds of the formula I, their use, in particular as active ingredients in pharmaceuticals, and pharmaceutical preparations comprising them.

20 Claims, No Drawings

UREA DERIVATIVES WITH ANTIPROTEOLYTIC ACTIVITY

This application is entitled to the benefit of earlier filed application EP 01115353.3, filed Jun. 26, 2001.

The present invention relates to compounds of the formula I,

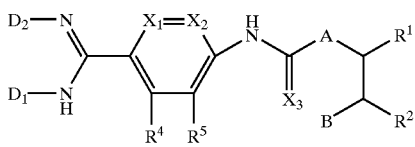

in which $R^1$, $R^2$, $R^4$, $R^5$, $D_1$, $D_2$, $X_1$, $X_2$, $X_3$, A and B have the meanings indicated below.

The compounds of the formula I are valuable pharmacologically active compounds. They act as serine protease inhibitors and especially exhibit a strong antithrombotic effect and are suitable, for example, for the therapy and prophylaxis of thromboembolic diseases and other diseases where serine protease activity is responsible for the disease. The preferred targets are the blood clotting enzymes, especially factor VIIa. Compounds of said invention can in general be applied in conditions in which an undesired activity of factor VIIa is present or for the cure or prevention of the disease of which an inhibition of factor VIIa is intended.

The invention furthermore relates to processes for the preparation of compounds of the formula I, their use, in particular as active ingredients in pharmaceuticals, and pharmaceutical preparations comprising them.

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs. Many significant disease states are related to abnormal haemostasis. For example, local thrombus formation due to rupture of atherosclerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel. There continues to be a need for safe and effective therapeutic anticoagulants to limit or prevent thrombus formation.

The widely used blood-clotting inhibitors like heparin and related sulfated polysaccharides like LMWH and heparin sulfate exert their anti-clotting effects by promoting the binding of a natural regulator of the clotting process, antithrombin III, to thrombin and to factor Xa. The inhibitory activity of heparin primarily is directed toward thrombin, which is inactivated approximately 100 times faster than factor Xa. Hirudin and hirulog are two additional thrombin-specific anticoagulants presently in clinical trials. However, these anticoagulants which inhibit thrombin also are associated with bleeding complications. Preclinical studies in baboons and dogs have shown that targeting enzymes involved at earlier stages of the coagulation cascade, such as factor Xa or factor VIIa, prevents clot formation without producing the bleeding side effects observed with direct thrombin inhibitors (L. A. Harker et al., Thromb. Hemostas. 74 (1995) 464).

Specific inhibition of the factor VIIa/tissue factor catalytic complex using monoclonal antibodies (WO-A-92/06711) or a protein such as chloromethyl ketone inactivated factor VIIa (WO-A-96/12800 and WO-A-97/47651) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty (L. A. Harker et al., Haemostasis 26 (1996) S1:76). Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition (L. A. Harker et al., Thromb. Hemostas. 74 (1995) 464).

A specific inhibitor of factor VIIa that has a favorable property profile would have substantial practical value in the practice of medicine. In particular, a factor VIIa inhibitor would be effective under circumstances where the present drugs of choice, like heparin and related sulfated polysaccharides, are ineffective or only marginally effective. Certain inhibitors of factor VIIa have already been described. EP-A-987274, for example, discloses compounds containing a tripeptide unit which inhibit factor VIIa. However, the property profile of these compounds is still not ideal, and there is a need for further low molecular weight factor VIIa-specific blood clotting inhibitors that are effective and do not cause unwanted side effects The present invention satisfies this need by providing novel factor VIIa activity urea derivatives of the formula I.

Thus, a subject of the present invention are compounds of the formula I,

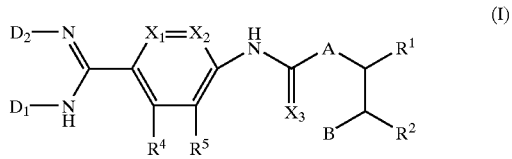

wherein $D_1$ and $D_2$ independently from one another are
1. hydrogen atom,
2. —C(O)—($C_1$–$C_6$)-alkyl,
3. —C(O)-aryl,
4. —C(O)—($C_1$–$C_6$)-alkyl-aryl,
5. —C(O)—O—($C_1$–$C_6$)-alkyl,
6. —C(O)—O—($C_1$–$C_6$)-alkyl-aryl,
7. —C(O)—O—($C_1$–$C_6$)-aryl or
8. —$NH_2$, or $D_1$ is hydrogen atom, when $D_2$ is
1. —OH,
2. —O—C(O)—($C_1$–$C_6$)-alkyl,
3. —O—C(O)-aryl,
4. —O—C(O)—($C_1$–$C_6$)-alkyl-aryl or
5. —$NH_2$, or $D_2$ is hydrogen atom, when $D_1$ is
1. —OH,
2. —O—C(O)—($C_1$–$C_6$)-alkyl,
3. —O—C(O)-aryl,
4. —O—C(O)—($C_1$–$C_6$)-alkyl-aryl or
5. —$NH_2$, or $D_1$ and $D_2$ together with the nitrogen atom to which they are attached form a cycle of the formula VIII

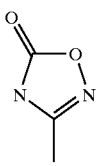

(VIII)

or $D_1$ and $R^4$ or $D_2$ and $R^4$ together form a cycle of the formulae VIIIa to VIIId,

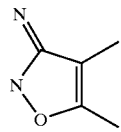

VIIIa

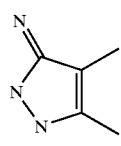

VIIIb

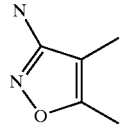

VIIIc

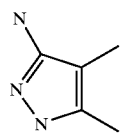

VIIId wherein $X_1$ and $X_2$ independently from one another are selected from the group consisting of a carbon atom substituted by $R^4$, wherein $R^4$ is as defined below, and a nitrogen atom, wherein $R^4$ and $R^5$ independently from one another are
1. hydrogen atom,
2. —$(C_1$-$C_6)$-alkyl,
3. —OH,
4. —O—$(C_1$-$C_6)$-alkyl,
5. halogen,
6. —$NH_2$ or
7. —$NO_2$, wherein $X_3$ is oxygen atom, sulfur atom or NH, wherein A is
1. —$X_4$—, wherein —$X_4$— is
   1.1 a covalent bond,
   1.2 —$CH_2$—,
   1.3 —CH(OH)—,
   1.4 —CH($NH_2$)—,
   1.5 —CH(COOH)—,
   1.6 —CH($CONH_2$)—,
   1.7 —CH($CH_2$—OH)—,
   1.8 —CH(—$CH_2$—$NH_2$)—,
   1.9 —CH(—$CH_2$—COOH)— or
   1.10 —CH(—$CH_2$—$CONH_2$)—,
2. —N($R^3$)—$X_4$—, wherein —$X_4$— is as defined above and wherein $R^3$ is
   a) hydrogen atom,
   b) —OH or
   c) —$NH_2$, or
3. —O—$X_4$—, wherein —$X_4$— is as defined above, $R^1$ and $R^2$ together with each carbon atoms to which they are attached form
1. -aryl, wherein aryl is unsubstituted or mono- or disubstituted independently of one another by $R^6$,
2. heteroaryl, wherein heteroaryl is unsubstituted or mono- or disubstituted independently of one another by $R^6$,
3. a 3- to 8-membered cyclic group, wherein said cyclic group is saturated or partially saturated and unsubstituted or mono- or disubstituted independently of one another by $R^6$ or =O, or
4. a 3- to 8-membered cyclic group, containing up to 1, 2, 3 or 4 heteroatoms chosen from nitrogen, sulfur or oxygen, wherein said cyclic group is saturated or partially saturated and unsubstituted or mono- or disubstituted independently of one another by $R^6$ or =O, wherein $R^6$ is
1. halogen,
2. —$(CH_2)_n$—OH, wherein n is the inter zero, 1 or 2,
3. —$(CH_2)_n$—O—$R^{10}$, wherein $R^{10}$ is —$(C_1$-$C_6)$-alkyl or —$(C_1$-$C_6)$-alkyl-aryl, and n is the integer zero, 1 or 2,
4. —$(CH_2)_n$—$COOR^{11}$, wherein $R^{11}$ is hydrogen atom, —$(C_1$-$C_6)$-alkyl or —$(C_1$-$C_6)$-alkyl-aryl, and n is the integer zero, 1 or 2,
5. —$(CH_2)_n$—C(O)N(H)$R^{12}$, wherein $R^{12}$ is hydrogen atom or —$(C_1$-$C_6)$-alkyl, and n is the integer zero, 1 or 2,
6. —$NO_2$,
7. —N(H)$R^{12a}$, wherein $R^{12a}$ is hydrogen atom, formyl, acetyl, sulfonylmethyl, amidosulfonyl or —$(C_1$-$C_6)$-alkyl,
8. —$CF_3$,
9. —$SO_2$—$R^{13}$, wherein $R^{13}$ is methyl, ethyl or —$NH_2$,
10. —CN,
11. —$(C_1$-$C_6)$-alkyl,
12. —$(C_1$-$C_6)$-alkyl-aryl,
13. -heteroaryl,
14. —$(C_1$-$C_6)$-alkyl-heteroaryl or
15. -heterocycloalkyl, B is 1. —N($R^7$)—(CH—($R^8$))$_p$-aryl, wherein aryl is unsubstituted or mono-, di- or trisubstituted independently of one another by
1.1. —$(C_1$-$C_6)$-alkyl, wherein alkyl is unsubstituted or mono-, di- or trisubstituted independently of one another by =O, =S, —O—$R^{10}$, halogen, aryl or heteroaryl,
1.2. —$(C_3$-$C_6)$-cycloalkyl, wherein cycloalkyl is unsubstituted or mono-, di- or trisubstituted independently of one another by =O, =S, —O—$R^{10}$, halogen, aryl or heteroaryl,
1.3. —$CF_3$,
1.4. —CN,
1.5. —$NO_2$,
1.6. halogen,
1.7. —C(O)—O—$R^{14}$, wherein $R^{14}$ is hydrogen atom or as defined for $R^6$ above,
1.8. —C(O)—$(C_0$-$C_6)$-alkyl, wherein alkyl is unsubstituted or mono-, di- or trisubstituted independently of one another as defined for $R^6$ above,
1.9. —O—$(C_1$-$C_6)$-alkyl, wherein alkyl is unsubstituted or mono-, di- or trisubstituted independently of one another as defined for $R^6$ above,
1.10. —O—$(C_1$-$C_6)$-alkyl-aryl, wherein alkyl and aryl independently of one another are unsubstituted or mono-, di- or trisubstituted independently of one another as defined for $R^6$ above, 1.11. —O—$(C_1-C_6)$-alkyl-heteroaryl, wherein alkyl and heteroaryl independently of one another are unsubstituted or mono-, di- or trisubstituted independently of one another as defined for $R^6$ above, 1.12. —O—C(O)—S—$(C_1-C_6)$-alkyl, 1.13 —O—C(O)—$(C_1-C_6)$-alkyl-aryl, wherein alkyl and aryl independently of one another are unsubstituted or mono-, di- or trisubstituted independently of one another as defined for $R^6$ above, 1.14 —O—C(O)—$(C_1-C_6)$-alkyl, wherein alkyl is unsubstituted or mono-, di- or trisubstituted independently of one another as defined for $R^6$ above, 1.15. —O—C(O)—$(C_1-C_6)$-alkyl-heteroaryl, wherein alkyl and heteroaryl independently of one another are unsubstituted or mono-, di- or trisubstituted independently of one another as defined for $R^6$ above, 1.16. —O—C(O)-aryl, wherein aryl is unsubstituted or mono-, di- or trisubstituted independently of one another as defined for $R^6$ above, 1.17. —O—C(O)-heteroaryl, wherein heteroaryl is unsubstituted or mono-, di- or trisubstituted independently of one another as defined for $R^6$ above, 1.18 —O—C(O)—NH—$(C_1-C_6)$-alkyl-aryl, wherein alkyl and aryl independently of one another are unsubstituted or mono-, di- or trisubstituted independently of one another as defined for $R^6$ above, 1.19 —O—C(O)—NH—$(C_1-C_6)$-alkyl, wherein alkyl is unsubstituted or mono-, di- or trisubstituted independently of one another as defined for $R^6$ above, 1.20. —O—C(O)—NH—$(C_1-C_6)$-alkyl-heteroaryl, wherein alkyl and heteroaryl independently of one another are unsubstituted or mono-, di- or trisubstituted independently of one another as defined for $R^6$ above, 1.21. —O—C(O)—NH-aryl, wherein aryl is unsubstituted or mono-, di- or trisubstituted independently of one another as defined for $R^6$ above, 1.22. —O—C(O)—NH-heteroaryl, wherein heteroaryl is unsubstituted or mono-, di- or trisubstituted independently of one another as defined for $R^6$ above, 1.23. aryl, wherein aryl is unsubstituted or mono-, di- or trisubstituted independently of one another as defined for $R^6$ above, 1.24. —O-aryl, wherein —O-aryl is unsubstituted or mono-, di- or trisubstituted independently of one another as defined for $R^6$ above, 1.25. heteroaryl, wherein heteroaryl is unsubstituted or mono-, di- or trisubstituted independently of one another as defined for $R^6$ above, 1.26. —O-heteroaryl, wherein —O-heteroaryl is unsubstituted or mono-, di- or trisubstituted independently of one another as defined for $R^6$ above, 1.27. —$(CH_2)_r$—$S(O)_s$—$R^{15}$, wherein —$R^{15}$ is
a) —OH, provided that s is only 2,
b) —$(C_1-C_6)$-alkyl, wherein alkyl is unsubstituted or mono-, di- or trisubstituted independently of one another as defined for $R^6$ above,
c) aryl, wherein aryl is unsubstituted or mono-, di- or trisubstituted independently of one another as defined for $R^6$ above,
d) —$(C_1-C_6)$-alkyl-aryl, wherein alkyl and aryl independently of one another are unsubstituted or mono-, di- or trisubstituted independently of one another as defined for $R^6$ above, or e) —$N(R^{16})_2$, wherein $R^{16}$ independently of one another are hydrogen atom or as defined for $R^{15}$ a) to $R^{15}$ d), provided that s is only 2, and r is the integer zero, 1, 2, or 3, s is the integer zero, 1 or 2, or 1.28. —$N(R^{17})_2$, wherein $R^{17}$ independently of one another are 1.28.1. hydrogen atom, 1.28.2.—$(C_1-C_6)$-alkyl, wherein alkyl is unsubstituted or mono-, di- or trisubstituted independently of one another as defined for the substituents 1.1. to 1.27. for aryl above, 1.28.3. aryl, wherein aryl is unsubstituted or mono-, di- or trisubstituted independently of one another as defined for the substituents 1.1. to 1.27. for aryl above or two adjacent carbon atoms of the aryl residue form a dioxolan residue, 1.28.4.—$(C_1-C_6)$-alkyl-aryl, wherein alkyl and aryl independently of one another are unsubstituted or mono-, di- or trisubstituted independently of one another as defined for the substituents 1.1. to 1.27. for aryl above or two adjacent carbon atoms of the aryl residue form a dioxolan residue, 1.28.5. heteroaryl, wherein heteroaryl is unsubstituted or mono-, di- or trisubstituted independently of one another as defined for the substituents 1.1. to 1.27. for aryl above or =O, 1.28.6.—$(C_1-C_6)$-alkyl-heteroaryl, wherein alkyl and heteroaryl independently of one another are unsubstituted or mono-, di- or trisubstituted independently of one another as defined for the substituents 1.1. to 1.27. for aryl above or =O, 1.28.7.—C(O)—$R^{18}$, wherein $R^{18}$ is
a) hydrogen atom,
b) —$(C_1-C_6)$-alkyl, wherein alkyl is unsubstituted or mono-, di- or trisubstituted independently of one another as defined for $R^6$ above,
c) aryl, wherein aryl is unsubstituted or mono-, di- or trisubstituted independently of one another as defined for $R^6$ above,
d) —$(C_1-C_6)$-alkyl-aryl, wherein alkyl and aryl independently of one another are unsubstituted or mono-, di- or trisubstituted independently of one another as defined for $R^6$ above, or
e) heteroaryl, wherein heteroaryl is unsubstituted or mono-, di- or trisubstituted independently of one another as defined for $R^6$ above,
f) —$(C_1-C_6)$-alkyl-heteroaryl, wherein alkyl and heteroaryl independently of one another are unsubstituted or mono-, di- or trisubstituted independently of one another as defined for $R^6$ above.

1.28.8.—C(S)—$R^{18}$, wherein $R^{18}$ is as defined above, 1.28.9.—C(O)—O—$R^{18}$, wherein $R^{18}$ is as defined above, 1.28.10. —C(O)—$N(R^{18})_2$, wherein $R^{18}$ independently of one another are as defined above, 1.28.11. —S(O)—$R^{18}$, wherein $R^{18}$ is as defined above, 1.28.12. —$S(O)_2$—$R^{18}$, wherein $R^{18}$ is as defined above, 1.28.13. —S(O)—$N(R^{18})_2$, wherein $R^{18}$ independently of one another are as defined above, or 1.28.14. —$S(O)_2$—$N(R^{18})_2$, wherein $R^{18}$ independently of one another are as defined above, or 1.28.15. —$(C_3-C_6)$-cycloalkyl, or 1.28.16. both $R^{17}$ residues form together with the nitrogen atom to which they each are bonded, a 3- to 8-membered cyclic group, containing up to 1, 2, 3 or 4 heteroatoms chosen from nitrogen, sulfur or oxygen, wherein said cyclic group is saturated or partially saturated, and wherein said cyclic group is unsubstituted or mono-, di- or trisubstituted independently of one another as defined for $R^6$ above or 1.29. —C(O)—N($R^{17}$)$_2$, wherein $R^{17}$ independently of one another are as defined for $R^{17}$ above, 2. —N($R^{17}$)$_2$, wherein $R^{17}$ independently of one another are as defined for $R^{17}$ above, 3. —O—(CH—($R^8$))$_p$-aryl, wherein $R^8$, p and aryl independently of one another are as defined for $R^8$, p and aryl above, provided that if there is a single bond between A and B, then A and B are in a cis-conformation to each other, p is the integer zero, 1 or 2, $R^7$ is
1.1 hydrogen atom,
1.2 —($C_1$–$C_6$)-alkyl or
1.3 —OH, $R^8$ is
1.1 hydrogen atom,
1.2 —($C_1$–$C_6$)-alkyl, wherein alkyl is unsubstituted or mono- to totally substituted by fluorine,
1.3 —($C_2$–$C_6$)-alkenyl, wherein alkenyl is unsubstituted or mono- di- or trisubstituted by fluorine,
1.4 —($C_2$–$C_6$)-alkinyl, wherein alkinyl is unsubstituted or mono- di- or trisubstituted by fluorine,
1.5 —($C_0$–$C_3$)-alkyl-($C_3$–$C_6$)-cycloalkyl, wherein alkyl is unsubstituted or mono- to totally substituted by fluorine,
1.6 —CN,
1.7 aryl, wherein aryl is unsubstituted or mono- or di-substituted as defined under 1.1. to 1.28. for aryl above,
1.8 heteroaryl, wherein heteroaryl is unsubstituted, mono- or di-substituted as defined under 1.1. to 1.28. for aryl above, or
1.9 —($C_0$–$C_2$)-alkyl-O—($C_1$–$C_6$)-alkyl, 2. —O—(CH—($R^8$))$_p$-aryl, wherein aryl, $R^8$ and p are as defined above, or 3. —N($R^7$)—(CH—($R^8$))$_p$-heteroaryl, wherein heteroaryl is unsubstituted or mono- or di-substituted as defined under 1.1. to 1.28. for aryl above and $R^7$, $R^8$ and p are as defined above, or 4. —S—(CH—($R^8$))$_p$-aryl, wherein aryl, $R^8$ and p are as defined above in all their stereoisomeric forms and mixtures thereof in any ratio, and their physiologically tolerable salts.

A further subject of the present invention are compounds of the formula I, wherein $D_1$ and $D_2$ are each hydrogen atom or $D_1$ is hydrogen atom and $D_2$ is —OH or $D_1$ is —OH and $D_2$ is hydrogen atom, $X_1$ and $X_2$ are independently from one another a —CH— residue or a nitrogen atom, $R^4$ and $R^5$ independently from one another are hydrogen atom or halogen, $X_3$ is oxygen atom, A is —NH— or —NH—$CH_2$—, $R^1$ and $R^2$ together with each carbon atoms to which they are attached form
1. phenyl, which is unsubstituted or substituted by halogen, —$CF_3$, —($CH_2$)—OH, —($CH_2$)—C(O)—O—$CH_3$, or —($CH_2$)—COOH,
2. thiophenyl, unsubstituted or substituted by —($CH_2$)—OH or —($CH_2$)—COOH or
3. naphthyl, unsubstituted or substituted by —($CH_2$)—OH or —($CH_2$)—COOH, B is
1. —N($R^7$)—(CH—($R^8$))$_p$-aryl, wherein aryl is indanyl, phenyl, tetralinyl or naphthalinyl, which are unsubstituted or mono- to di-substituted independently of one another by
1.1. —C(O)—N($R^{17}$)$_2$, wherein $R^{17}$ independently of one another are
1.1.1. hydrogen atom,
1.1.2. phenyl, wherein phenyl is unsubstituted or mono-, di- or trisubstituted independently of one another by
1.1.2.1 —($C_1$–$C_6$)-alkyl, wherein alkyl is unsubstituted or mono-, di- or trisubstituted independently of one another by halogen,
1.1.2.2. halogen, out of the group Cl, F and J,
1.1.2.3. —C(O)—O—$R^{14}$, wherein $R^{14}$ is hydrogen atom or methyl or ethyl,
1.1.2.4. —O—($C_1$–$C_3$)-alkyl, wherein each alkyl residue is unsubstituted or mono-, di- or trisubstituted independently of one another by Cl, F and J,
1.1.2.5. —O—($C_1$–$C_3$)-alkyl-phenyl, wherein phenyl and alkyl independently of one another are unsubstituted or mono-, di- or trisubstituted independently of one another by Cl, F and J,
1.1.2.6. phenyl, wherein phenyl is unsubstituted or mono-, di- or trisubstituted independently of one another by Cl, F and J,
1.1.2.7. —O-phenyl, wherein phenyl is unsubstituted or mono-, di- or trisubstituted independently of one another by Cl, F and J, or
1.1.2.8. —($CH_2$)$_r$—S(O)$_s$—$R^{15}$, wherein —$R^{15}$ is methyl, ethyl or —N($R^{16}$)$_2$, wherein $R^{16}$ methyl or ethyl, and r is the integer zero or 1, s is the integer 1 or 2, or two adjacent carbon atoms of the phenyl residue form a dioxolan residue, 1.1.3. —($C_1$–$C_6$)-alkyl-phenyl, wherein alkyl and phenyl independently of one another are unsubstituted or mono-, di- or trisubstituted independently of one another as defined for the substituents 1.1.2.1. to 1.1.2.8. for phenyl above or two adjacent carbon atoms of the phenyl residue form a dioxolan residue, 1.1.4. heteroaryl, wherein heteroaryl is out of the group imidazolyl, isobenzofuran, benzimidazolyl, morpholinyl, oxazolyl, benzoxazolyl, thiazolyl, thiophenyl, indazolyl, benzothiazolyl, indolyl, indolinyl, or pyridinyl and is unsubstituted or mono-, di- or trisubstituted independently of one another by phenyl or as defined for the substituents 1.1.2.1. to 1.1.2.8. for phenyl above or =O, 1.1.5. —($C_1$–$C_6$)-alkyl-heteroaryl, wherein heteroaryl is out of the group imidazolyl, isobenzofuranyl, benzimidazolyl, morpholinyl, oxazolyl, benzoxazolyl, thiazolyl, thiophenyl, indazolyl, benzothiazolyl, indolyl, indolinyl, or pyridinyl and wherein alkyl and heteroaryl independently of one another are unsubstituted or mono-, di- or trisubstituted independently of one another by phenyl or as defined for the substituents 1.1.2.1. to 1.1.2.8. for phenyl above or =O, 1.1.6. both $R^{17}$ residues form, together with the nitrogen atom to which they each are bonded, a 3- to 8-membered cyclic group out of the group morpholinyl, indazolyl, indolyl, indolinyl, aziridinyl, pyrazolyl, pyrazinolyl, pyrrolidinyl, pyrrolinyl, piperidinyl, piperazinyl, imidazolinyl, imidazolidinyl, thiomorpholinyl, pyridazinolidinyl, pyridazinolinyl, isoindolyl and wherein said cyclic group is unsubstituted or mono-, di- or trisubstituted independently of one another by phenyl or as defined for the substituents 1.1.2.1. to 1.1.2.8. for phenyl above or =O, or 1.1.7. —($C_3$–$C_6$)-cycloalkyl,
1.2. Cl,
1.3. F,
1.4. Br,
1.5. —$CF_3$,
1.6. —$NO_2$,
1.7. phenyl,
1.8. phenyloxy,
1.9. benzyloxy,
1.10. methyl,
1.11. methoxy,
1.12. carboxyl,
1.13 carboxylalkyl or
1.14. carboxylalkylphenyl,
p is the integer zero or 1,
$R^7$ is hydrogen atom,
$R^8$ is
1.1 hydrogen atom,
1.2 —($C_1$–$C_2$)-alkyl, unsubstituted or all hydrogen atoms are substituted by fluorine
1.3 —CN,
1.4 phenyl, wherein phenyl is unsubstituted or mono- or di-substituted by methoxy or halogen,
1.5 —($C_0$–$C_2$)-alkyl-O—($C_1$–$C_4$)-alkyl,
1.6 cyclopropylmethyl, or
1.7 ethinyl,
2. —O—(CH—($R^8$))$_p$-phenyl, wherein $R^8$ and p are as defined above, or
3. —N($R^{17}$)$_2$, wherein $R^{17}$ independently of one another are hydrogen atom or heteroaryl residue out of the group aziridine, oxirane, azetidine, pyrrole, furan, thiophene, dioxole, imidazole, pyrazole, oxazole, isoxazole, thiazole, isothiazole, thiadiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3, 5-triazine, azepine, 1,2-diazepine, 1,3-diazepine, 1,4-diazepine, indole, isoindole, benzofuran, isobenzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines and pyridopyrimidines, which is unsubstituted or mono substituted by Br, Cl, F, —$CF_3$, —$NO_2$, =O, phenyl, phenoxy, methyl, benzyl, benzyloxy, methyl, methoxy, carboxy, carboxyalkyl or carboxyalkylaryl.

A further subject of the present invention are compounds of the formula I, wherein
$D_1$ and $D_2$ are each hydrogen atom
$X_1$ and $X_2$ are each a —CH— residue,
$R^4$ and $R^5$ are each hydrogen atom,
$X_3$ is an oxygen atom,
A is —NH— or —NH—$CH_2$—,
$R^1$ and $R^2$ together with each carbon atoms to which they are attached form
1. phenyl, which is unsubstituted or substituted by halogen, —$CF_3$ or —($CH_2$)—C(O)—O—$CH_3$,
2. thiophene, substituted by —($CH_2$)—C(O)—O—$CH_3$ or —($CH_2$)—COOH or
3. naphthyl,
B is
1. —N($R^7$)—(CH—($R^8$))$_p$-phenyl, wherein phenyl is unsubstituted or mono- or di-substituted independently of one another by
1.1. —C(O)—N($R^{17}$)$_2$, wherein $R^{17}$ independently of one another are
1.1.1. hydrogen atom,
1.1.2. phenyl, wherein phenyl is unsubstituted or monosubstituted by
1.1.2.1 —($CH_2$)$_r$—S(O)$_s$—$R^{15}$, wherein —$R^{15}$ is methyl or —N($R^{16}$)$_2$, wherein $R^{16}$ methyl, and
r is the integer zero or 1,
s is the integer 1 or 2, or
1.1.3. —($C_1$–$C_2$)-alkyl-phenyl, wherein phenyl is unsubstituted or mono-substituted as defined for the substituent 1.1.2.1. for phenyl above,
1.1.4. heteroaryl, wherein heteroaryl is benzoxazolyl, morpholinyl, isobenzofuran, thiophenyl or pyridinyl and is unsubstituted or monosubstituted by phenyl or =O, or
1.1.5. —($C_3$–$C_6$)-cycloalkyl,
p is the integer zero or 1,
$R^7$ is hydrogen atom,
$R^8$ is hydrogen atom or methyl, or
2. —N($R^{17}$)$_2$, wherein $R^{17}$ independently of one another are hydrogen atom or pyridinyl, which is unsubstituted or mono substituted by benzyl.

As used herein, the term alkyl is to be understood in the broadest sense to mean hydrocarbon residues which can be linear, i.e. straight-chain, or branched and which can be acyclic or cyclic groups or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another group, for example in an alkoxy group (alkyl-O—), an alkoxycarbonyl group or an arylalkyl group. Examples of alkyl groups containing 1, 2, 3, 4, 5 or 6 carbon atoms are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. The term "($C_0$–$C_6$)-alkyl" is an alkyl group containing zero, 1, 2, 3, 4, 5 or 6 carbon atoms; in case of "($C_0$)-alkyl" a covalent bond is formed.

Unsaturated alkyl groups are, for example, alkenyl groups such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl groups such as ethynyl, 1-propynyl, 2-propynyl (=propargyl) or 2-butynyl. Alkyl groups can also be unsaturated when they are substituted.

Examples of cyclic alkyl groups are cycloalkyl groups containing 3, 4, 5, 6 or 7 ring carbon atoms like cyclopropyl, cyclobutyl, cyclopentyl or cyclohexyl, which can also be substituted and/or unsaturated. Unsaturated cyclic alkyl groups and unsaturated cycloalkyl groups like, for example, cyclopentenyl or cyclohexenyl can be bonded via any carbon atom. The term alkyl as used herein also comprises cycloalkyl-substituted alkyl groups like cyclopropylmethyl-, cyclobutylmethyl-, cyclopentylmethyl-, 1-cyclopropyl-ethyl-, 1-cyclobutylethyl-, 1-cyclopentylethyl-, 2-cyclopropylethyl-, 2-cyclobutylethyl-, 2-cyclopentylethyl-, 3-cyclopropylpropyl-, 3-cyclobutylpropyl-, etc. in which groups the cycloalkyl subgroup as well as acyclic subgroup can be unsaturated and/or substituted.

Of course, a cyclic alkyl group has to contain at least three carbon atoms, and an unsaturated alkyl group has to contain at least two carbon atoms. Thus, a group like $(C_1-C_6)$-alkyl is to be understood as comprising, among others, saturated acyclic $(C_1-C_6)$-alkyl, $(C_3-C_7)$-cycloalkyl, cycloalkyl-alkyl groups like $(C_3-C_7)$-cycloalkyl-$(C_1-C_3)$-alkyl- wherein the total number of carbon atoms can range from 4 to 7, and unsaturated $(C_2-C_6)$-alkyl like $(C_2-C_6)$-alkenyl or $(C_2-C_6)$-alkynyl. Similarly, a group like $(C_1-C_4)$-alkyl is to be understood as comprising, among others, saturated acyclic $(C_1-C_4)$-alkyl, $(C_3-C_4)$-cycloalkyl, cyclopropyl-methyl-, and unsaturated $(C_2-C_4)$-alkyl like $(C_2-C_4)$-alkenyl or $(C_2-C_4)$-alkynyl.

The term aryl refers to a monocyclic or polycyclic hydrocarbon residue in which at least one carbocyclic ring is present that has a conjugated pi electron system. A aryl group contains from 6 to 14 ring carbon atoms. Examples of aryl groups are phenyl, naphthyl, indanyl, tetralinyl, biphenylyl, fluorenyl or anthracenyl. Preferred $(C_6-C_{10})$-aryl groups are phenyl or naphthyl. Unless stated otherwise, and irrespective of any specific substituents bonded to aryl groups which are indicated in the definition of the compounds of the formula I, aryl groups, for example phenyl, naphthyl or fluorenyl, can in general be unsubstituted or substituted by one or more, for example one, two or three, identical or different substituents. Aryl groups can be bonded via any desired position, and in substituted aryl groups the substituents can be located in any desired position.

In mono substituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position. Naphthyl groups can be 1-naphthyl and 2-naphthyl. In substituted naphthyl groups the substituents can be located in any positions, for example in mono substituted 1-naphthyl groups in the 2-, 3-, 4-, 5-, 6-, 7-, or 8-position and in mono substituted 2-naphthyl groups in the 1-, 3-, 4-, 5-, 6-, 7-, or 8-position. Biphenylyl groups can be biphenyl-2-yl, biphenyl-3-yl or biphenyl-4-yl. Fluorenyl groups can be bonded via the 1-, 2-, 3-, 4- or 9-position. In mono substituted fluorenyl groups bonded via the 9-position the substituent is preferably present in the 1-, 2-, 3- or 4-position.

The above statements relating to aryl groups correspondingly apply to divalent groups derived from aryl groups, i.e. to arylene groups like phenylene which can be unsubstituted or substituted 1,2-phenylene, 1,3-phenylene or 1,4-phenylene, or naphthylene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl or 2,7-naphthalenediyl. The above statements also correspondingly apply to the aryl subgroup in arylalkyl-groups. Examples of arylalkyl-groups which can also be unsubstituted or substituted in the aryl subgroup as well as in the alkyl subgroup, are benzyl, 1-phenylethyl, 2-phenylethyl, 3-phenylpropyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, or 9-fluorenylmethyl. All the above explanations also corresponding apply to aromatic rings which may be condensed (or fused) to a ring formed.

The term "heteroaryl" comprises groups containing 3, 4, 5, 6, 7, 8, 9 or 10 ring atoms in the parent monocyclic or bicyclic heterocyclic ring system. In monocyclic heteroaryl groups the heterocyclic ring preferably is a 3-membered, 4-membered, 5-membered, 6-membered, or 7-membered ring, particularly preferably a 5-membered or 6-membered ring. In bicyclic heteroaryl groups preferably two fused rings are present one of which is a 5-membered ring or 6-membered heterocyclic ring and the other of which is a 5-membered or 6-membered heterocyclic or carbocyclic ring, i.e. a bicyclic ring heteroaryl preferably contains 8, 9 or 10 ring atoms, particularly preferably 9 or 10 ring atoms.

Heteroaryl comprises saturated heterocyclic ring systems which do not contain any double bonds within the rings, as well as unsaturated heterocyclic ring systems including mono-unsaturated and poly-unsaturated heterocyclic ring systems which contain one or more, for example one, two, three, four or five, double bonds within the rings provided that the resulting system is stable. Unsaturated rings may be partially unsaturated or non-aromatic, or they may be aromatic, i.e. double bonds within the rings in the heteroaryl group may be arranged in such a manner that a conjugated pi electron system results. Aromatic rings in a heteroaryl group may be 5-membered or 6-membered rings, i.e. aromatic groups in a heteroaryl group contain 5 to 10 ring atoms.

Aromatic rings in a heteroaryl group thus comprise 5-membered and 6-membered monocyclic heterocycles and bicyclic heterocycles composed of two 5-membered rings, one 5-membered ring and one 6-membered ring, or two 6-membered rings. In bicyclic aromatic groups in a heteroaryl group one or both rings may contain heteroatoms. Aromatic heteroaryl groups may also be referred to by the customary term heteroaryl for which all the definitions and explanations above and below relating to heteroaryl correspondingly apply. These explanations relating to the saturation/unsaturation in heterocyclic ring systems representing the heteroaryl group corresponding apply to any other heterocyclic ring system that can be present in a compound of the formula I, for example to a ring formed by $R^1$ and $R^2$ together with the carbon atom to which these groups are bonded, and the ring systems that may be condensed to this ring.

In a heteroaryl group and any other heterocyclic group preferably 1 or 2 identical or different ring heteroatoms selected from nitrogen, oxygen and sulfur atoms are present. In general, the ring heteroatoms can be present in any desired combination and in any desired positions with respect to each other provided that the resulting heterocyclic system is known in the art and is stable and suitable as a subgroup in a drug substance. Examples of parent structures of heterocycles from which the heteroaryl group any other heterocyclic groups can be derived are aziridine, oxirane, azetidine, pyrrole, furan, thiophene, dioxole, imidazole, pyrazole, oxazole, isoxazole, thiazole, isothiazole, thiadiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, etc. as well as ring systems which result from the listed heterocycles by fusion (or condensation) of a carbocyclic ring, for example benzo-fused, cyclopenta-fused, cyclohexa-fused or cyclohepta-fused derivatives of these heterocycles.

The fact that many of the before-listed names of heterocycles are the chemical names of unsaturated or aromatic ring systems does not imply that the heteroaryl groups and other heterocyclic groups could only be derived from the respective unsaturated ring system. The names here only serve to describe the ring system with respect to ring size and the number of the heteroatoms and their relative positions.

The heteroaryl group and other any other heterocyclic group may be bonded via any ring carbon atom, and in the case of nitrogen heterocycles via any suitable ring nitrogen atom, if applicable. Thus, for example, a pyrrolyl group can be pyrrol-1-yl, pyrrol-2-yl or pyrrol-3-yl, a pyrrolidinyl group can be pyrrolidin-1-yl (=pyrrolidino), pyrrolidin-2-yl or pyrrolidin-3-yl, a pyridinyl group can be pyridin-2-yl, pyridin-3-yl or pyridin-4-yl, a piperidinyl group can be piperidin-1-yl (=piperidino), piperidin-2-yl, piperidin-3-yl or piperidin-3-yl. Furyl can be furan-2-yl or fur-3-yl, thienyl can be thiophen-2-yl or thiophen-3-yl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=pyrimidin-6-yl) or pyrimidin-5-yl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazol groups can be bonded via the 2-position and via any of the positions 4, 5, 6, and 7. Quinolinyl can be quinolin-2-yl, quinolin-3-yl, quinolin-4-yl, quinolin-5-yl, quinolin-5-yl, quinolin-7-yl or quinolin-8-yl, isoqinolinyl can be isoquinolin-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

The term "3- to 8-membered cyclic group, wherein said cyclic group is saturated or partially saturated" refers to cyclic alkyl groups such as cycloalkyl groups containing 3, 4, 5, 6, 7 or 8 ring carbon atoms like cyclopropyl, cyclobutyl, cyclopentyl or cyclohexyl, which can also be substituted and/or unsaturated. Unsaturated cyclic alkyl groups and unsaturated cycloalkyl groups are for example, cyclopentenyl or cyclohexenyl.

The term "3- to 8-membered cyclic group, containing up to 1, 2, 3 or 4 heteroatoms chosen from nitrogen, sulfur or oxygen, wherein said cyclic group is saturated or partially saturated" refers to a heteroaryl group which is saturated or partially unsaturated, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), 2,3-dihydrobenzo[1,4]dioxine, 3,4-dihydro-2H-benzo[1,4]oxazine, perhydro-1,4-thiazine (=thiomorpholine), perhydroazepine, indoline, isoindoline, 1,2,3,4-tetrahydroquinoline, 1,2,3,4-tetrahydroisoquinoline, etc.

The term "halogen" is understood as meaning fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The term "patient" refers to animals, preferable mammals, and more preferably humans.

Physiologically tolerable salts of the compounds of formula I are nontoxic salts that are physiologically acceptable, in particular pharmaceutically utilizable salts. Such salts of compounds of the formula I containing acidic groups, for example a carboxy group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)-amine. Basic groups contained in the compounds of the formula I, for example amino groups or amidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. The present invention also includes acid addition salts of compounds of the formula I which contain, for example, two basic groups, with one or two acid equivalents.

Salts of compounds of the formula I can be obtained by customary methods known to those skilled in the art, for example by combining a compound of the formula I with an inorganic or organic acid or base in a solvent or diluent, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The anions of the mentioned acids that may be present in acid addition salts of the compounds of the formula I, are also examples of anions that may be present in the compounds of the formula I if they contain one or more positively charged groups like trialkylammonio-substituents, i.e. groups of the formula $(alkyl)_3N^+$ bonded via the positively charged nitrogen atom, or quaternized ring nitrogen atoms in heterocyclic groups. In general a compound of the formula I contains one or more physiologically tolerable anions or anion equivalents as counterions if it contains one or more permanently positively charged groups like trialkylammonio. Compounds of the formula I which simultaneously contain a basic group or a positively charged group and an acidic group, for example an amidino group and a carboxy group, can also be present as zwitterions (betaines) which are likewise included in the present invention.

The present invention furthermore includes all solvates of compounds of the formula I, for example hydrates or adducts with alcohols. The invention also includes derivatives and modifications of the compounds of the formula I, for example prodrugs, protected forms and other physiologically tolerable derivatives including esters and amides of acid groups, as well as active metabolites of the compounds of the formula I.

The present invention also relates to processes of preparation by which the compounds of the formula I are obtainable. The compounds of the formula I can generally be prepared by linkage of two or more fragments (or building blocks) which can be derived retrosynthetically from the formula I. In the preparation of the compounds of the formula I it can generally be advantageous or necessary in the course of the synthesis to introduce functional groups which could lead to undesired reactions or side reactions in a synthesis step in the form of precursors which are later converted into the desired functional groups. As examples of precursor groups cyano groups may be mentioned which may later be converted into amidino groups, or nitro groups which may be converted into amino groups. Protecting groups (or blocking groups) that may be present on functional groups include allyl, tert-butyl, benzyl, allyloxycarbonyl (Alloc), tert-butoxycarbonyl (Boc), benzyloxycarbonyl (Z) and 9-fluorenylmethoxycarbonyl (Fmoc) as protecting groups for hydroxy, carboxylic acid, amino and amidino groups.

In particular, in the preparation of the compounds of the formula I building blocks can be connected by performing one or more condensation reactions and/or alkylations and/or addition reactions such as amide couplings, i.e. by forming an amide bond between a carboxylic acid group of one building block and an amino group of another building block or forming an urea by reacting e.g. an isocyanate/isothiocyanate and an amino compound of either side of the carbonyl group.

For example compounds of the formula I can be prepared by linking the building blocks of the formulae VI, VII and IX

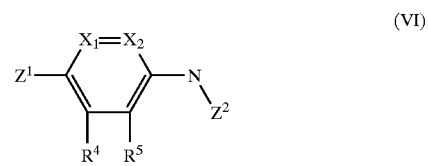

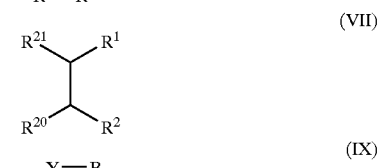

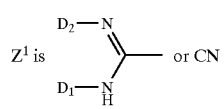 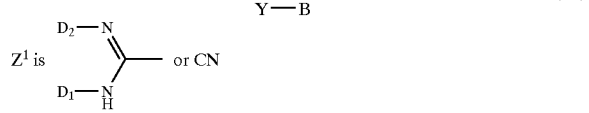

wherein $R^{21}$ is —OH, —$NR^7$, F or —SH, an acid chloride, an ester, such as a —$(C_1-C_4)$-alkyl ester, or an activated ester, or a mixed anhydride, or an isocyanate or any other activated species resulting from the reaction of the carboxylic acid with coupling reagents, or amines with carbonylation reagents, Y is hydrogen atom, $R^{20}$ is —OH, —$NR^7$, F or —SH, and $Z^2$ is hydrogen atom, part of an isocyanate or part of a chlorocarbonyl or imidazolide or related activated species, and $R^1$, $R^2$, $R^4$, $R^5$, $R^7$, $D_1$, $D_2$, $X_1$, $X_2$, $X_3$, A and B are as defined for formula I, by means of forming in a manner known per se a bond between the $Z^2$ derivative depicted in formula VI and the $R^{21}$ group depicted in formula VII and a bond between the Y derivative depicted in formula IX and the $R^{20}$ group depicted in formula VII.

It might be useful to start the synthesis with a so-called central scaffold, e.g. as shown by formulae II to V,

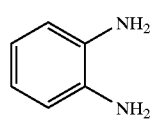

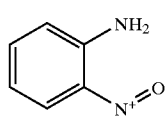

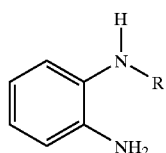

-continued

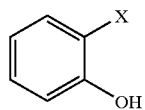
(V)

wherein X is NH$_2$, NO$_2$ or NHR.

For example, these central scaffolds are represented by diamino or hydroxyamino aryls, for the functional groups optionally being protected or in such a kind modified, that easy interconversion to amino or alcohol groups is possible during synthesis. Thus instead of amino groups, nitro precursors e.g. as represented by formula III or protected/modified diamino forms as represented by formula V, which itself are preferably prepared from compounds of formula III, can be used as starting materials. Of course, it is as well possible, to start with any of the hydroxy compounds shown in formula V. Instead of phenyl compounds of the kind shown any other analogous aryl or heteroaryl compound might be used.

One of these or related central scaffolds are either first reacted with a suitable derivative of the side chain B (in formula I), as represented by the respective halogen compounds, i.e. the bromides, chlorides, or activated alcohols like tosylates, mesylates or trifluoromethansulfonates, giving the alkylation products of the amine or alcohol moiety. A single representative example is shown below. Instead of alkylation reactions or the Williamson synthesis the Mitsunobu reaction might be used especially for the formation of an ether bond between the phenol and an aliphatic secondary alcohol/thiol bearing the or a part of the side chain B.

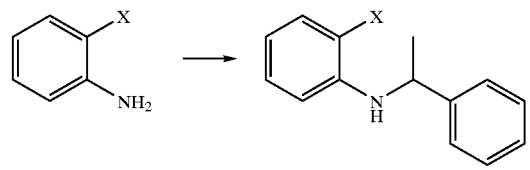

Then formation of the e.g. urea, thiourea or amide will be accomplished, optionally after protective group cleavage or interconversion of the second functional group of the central scaffold. If e.g. the simple urea derivative is desired, this will be the 4-cyanophenylisocyanate. Instead of the shown phenyl derivative any other modified diamine or hydroxyamine or analogously protected or interconvertable precursors might be used.

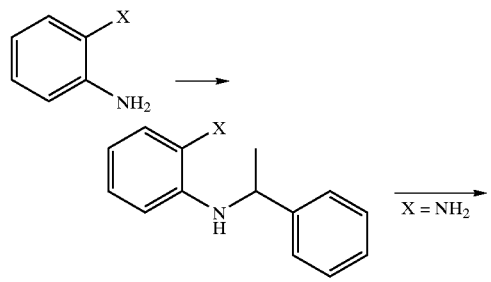

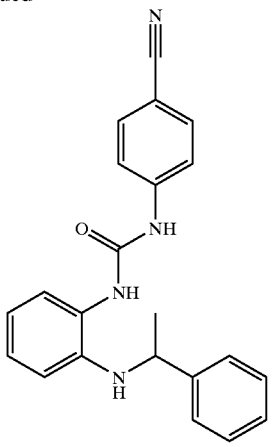

It might sometimes be more convenient or efficient, first to make the urea, thiourea or amide by reacting the central scaffold with the e.g. 4-cyanophenylisocyanat or -thiocyanate and then to alkylate or etherify by using the suitable method.

Of course, any other method for the synthesis of the N- or O-alkylated intermediates might be used. For the synthesis of the ureas, thioureas, amides or carbamates, any other methods known to the person skilled in the art might be applied, too: for example, any of the two amine components (if the urea is desired) can be preactivated with phosgene, thiophosgene, diphosgene, triphosgene, activated chloroformates, carbonyl diimidazole (or the thio analog) or related reagents and then, usually in a one-pot-reaction, the second amine be added or the respective alcohol can be preactivated with a suitable reagent like phosgene or CDI and then be reacted with e.g. 4-cyanoaniline, or with a protected amidino-aniline derivative.

Resulting nitrile precursors (preferably after assembling both part A and B to the central scaffold) have to be transformed to the amidines, hydroxyamidines, amidrazones or related functional groups. For amidine synthesis the Pinner reaction is quite useful; first, an imino ester will be prepared with alcoholic HCl; then, nucleophilic replacement with NH$_3$ or any suitable amine nucleophil gives the amidine; if hydrazine will be used, the product is an amidrazone. Alternatively, hydroxylamine can be added to the nitrile (in situ liberation from the e.g. hydrochloride with base, e.g, triethylamine). The resulting hydroxyamidine can be used as an prodrug, or hydrogenated with e.g. raney nickel or palladium on charcoal resulting in the amidine, too. Amidines or hydroxyamidines can be modified by methods known to persons skilled in the art (e.g., prodrug synthesis or introduction of protective groups).

A great variety of central scaffolds can be used in the preparation of the compounds of the formula I; for the case, that further substituents/side chains are attached or additional reactive centers (N, NH, O, OH, COOH etc) are part of the molecule, it is necessary to choose the right strategy with respect to protective groups and sequence of synthetic steps and functional group transformations.

The activation reactions and coupling reactions are usually performed in the presence of an inert solvent (or diluent), for example in the presence of an aprotic solvent like dimethylformamide (DMF), tetrahydrofuran (THF), dichloromethane (DCM), N-methylpyrrolidone (NMP), dimethylsulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and be, for example, from about −20° C. to the boiling temperature of the solvent or diluent. Also depending on the specific process, it may be necessary or advantageous to add in a suitable amount one or more auxiliary agents, for example a base like a tertiary amine, such as triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, J. March, Advanced Organic Chemistry, 4th ed., John Wiley & Sons, 1992; or Houben-Weyl, Methoden der organischen Chemie [Methods of Organic Chemistry], Georg Thieme Verlag. For the Mitsunobu reaction cf. Organic Reactions, Vol. 42, Wiley, 1992.

Protective groups that may still be present in the products obtained in the coupling reaction are then removed by standard procedures. For example, tert-butyl protecting groups, in particular a tert-butoxycarbonyl group which is a protected form of an amidino group, can be deprotected, i.e. converted into the amidino group, by treatment with trifluoroacetic acid. As already explained, after the coupling reaction also functional groups can be generated from suitable precursor groups. In addition, a conversion into a physiologically tolerable salt or a prodrug of a compound of the formula I can then be carried out by known processes.

In general, a reaction mixture containing a final compound of the formula I or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

The compounds of the formula I, which on account of its chemical structure occurs in enantiomeric forms, if enantiomerically pure starting materials cannot be used, can be resolved into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups. On the other hand, enantioselective synthesis might be another option to get enantiomerically pure compounds.

The compounds of the formula I can be isolated either in free form or, in the case of the presence of acidic or basic groups, converting it into physiologically tolerable salts. The preparation of physiologically tolerable salts of compounds of the formula I capable of salt formation, including their stereoisomeric forms, is carried out in a manner known per se. With basic reagents such as hydroxides, carbonates, hydrogencarbonates, alkoxides and also ammonia or organic bases, for example trimethyl- or triethylamine, ethanolamine or triethanolamine or alternatively basic amino acids, for example lysine, ornithine or arginine, the carboxylic acids form stable alkali metal, alkaline earth metal or optionally substituted ammonium salts. If the compounds of the formula I contain basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic or trifluoroacetic acid are suitable.

The invention also relates to pharmaceuticals which comprise an efficacious amount of at least one compound of the formula I and/or of a physiologically tolerable salt of the compounds of the formula I and/or an optionally stereoisomeric form of the compounds of the formula I, together with a pharmaceutically suitable and physiologically tolerable excipient, additive and/or other active compounds and auxiliaries.

The compounds of the present invention inhibit the activity of the blood coagulation enzyme factor VIIa either directly, within the prothrombinase complex or as a soluble subunit, or indirectly, by inhibiting the assembly of factor VIIa into the prothrombinase complex.

Because of their factor VIIa inhibitory activity the compounds of the formula I are useful pharmacologically active compounds which are suitable, for example, for influencing blood coagulation (or blood clotting) and fibrinolysis and for the treatment, including therapy and prophylaxis, of diseases such as, for example, cardiovascular disorders, thromboembolic diseases or restenoses. The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration and which contain, as active constituent, an effective amount of at least one compound of the formula I and/or its physiologically tolerable salts and/or its prodrugs and a pharmaceutically acceptable carrier.

The present invention therefore also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of factor VIIa or for influencing blood coagulation or fibrinolysis or for the treatment, including therapy and prophylaxis, of the diseases mentioned above or below, for example for the production of pharmaceuticals for the treatment of cardiovascular disorders, thromboembolic diseases or restenoses. The invention also relates to the use of the compounds of the formula I and/or their physiologically tolerable salts and/or their prodrugs for the inhibition of factor VIIa or for influencing blood coagulation or fibrinolysis or for the treatment of the diseases mentioned above or below, for example for use in the treatment, including therapy and prophylaxis, of cardiovascular disorders, thromboembolic diseases or restenoses, and to methods of treatment aiming at such purposes including methods for said therapies and prophylaxes. The present invention furthermore relates to pharmaceutical preparations (or pharmaceutical compositions) which contain an effective amount of at least one compound of the formula I and/or its physiologically tolerable salts and/or its prodrugs and a pharmaceutically acceptable carrier, i.e. one or more pharmaceutically acceptable carrier substances (or vehicles) and/or additives (or excipients).

The present invention further relates to methods of inhibiting factor VIIa, in a patient in need thereof, comprising administering to said patient a pharmaceutically effective amount of a compound of the present invention.

The present invention further relates to methods of inhibiting blood clotting, in a patient in need thereof, comprising administering to said patient a pharmaceutically effective amount of a compound of the present invention.

The present invention further relates to methods of inhibiting inflammatory responses, in a patient in need thereof, comprising administering to said patient a pharmaceutically effective amount of a compound of the present invention.

The present invention further relates to methods of treating a cardiovascular disorders, in a patient in need thereof, comprising administering to said patient a pharmaceutically effective amount of a compound of the present invention.

The present invention further relates to methods of treating thromboembolic disease, in a patient in need thereof, comprising administering to said patient a pharmaceutically effective amount of a compound of the present invention.

The present invention further relates to methods of treating restenosis, in a patient in need thereof, comprising administering to said patient a pharmaceutically effective amount of a compound of the present invention.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances arid/or additives being used in addition to the compound(s) of the formula I and/or its (their) physiologically tolerable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 to about 1000 mg, preferably from about 1 to about 500 mg.

In addition to the active ingredients of the formula I and/or their physiologically acceptable salts and/or prodrugs and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. In case a pharmaceutical preparation contains two or more compounds of the formula I the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or its physiologically tolerable salts and/or its prodrugs, the pharmaceutical preparations can also contain one or more other therapeutically or prophylactically active ingredients.

As inhibitors of factor VIIa the compounds of the formula I and their physiologically tolerable salts and their prodrugs are generally suitable for the therapy and prophylaxis of conditions in which the activity of factor VIIa plays a role or has an undesired extent, or which can favorably be influenced by inhibiting factor VIIa or decreasing its activity, or for the prevention, alleviation or cure of which an inhibition of factor VIIa or a decrease in its activity is desired by the physician. As inhibition of factor VIIa influences blood coagulation and fibrinolysis the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

Conditions in which a compound of the formula I and/or a physiologically tolerable salt thereof and/or a prodrug thereof can be favorably used include, for example, cardiovascular disorders, thromboembolic diseases or complications associated, for example, with infection or surgery. The compounds of the present invention can also be used to reduce an inflammatory response. Examples of specific disorders for the treatment, including therapy and prophylaxis, of which the compounds of the formula I can be used are coronary heart disease, myocardial infarction, angina pectoris, vascular restenosis, for example restenosis following angioplasty like PTCA, adult respiratory disstress syndrome, multi-organ failure, stroke and disseminated intravascular clotting disorder. Examples of related complications associated with surgery are thromboses like deep vein and proximal vein thrombosis which can occur following surgery. In view of their pharmacological activity the compounds of the invention can replace other anticoagulant agents such as heparin. The use of a compound of the invention can result, for example, in a cost saving as compared to other anticoagulants.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I and its salts can be used for diagnostic purposes, for example in in vitro diagnoses, and as an auxiliary or tool in biochemical investigations. For example, a compound of the formula I can be used in an assay to identify the presence of factor VIIa or to isolate factor VIIa in a substantially purified form. A compound of the invention can be labeled with, for example, a radioisotope, and the labeled compound bound to factor VIIa is then detected using a routine method useful for detecting the particular label. Thus, a compound of the formula I or a salt thereof can be used advantageously as a probe to detect the location or amount of factor VIIa activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

It is understood that modifications that do not substantially affect the activity of the various embodiments of this invention are included within the invention disclosed herein. Accordingly, the following examples are intended to illustrate but not limit the present invention.

EXAMPLES

Abbreviations

| | |
|---|---|
| Boc | tert. Butyl oxycarbonyl |
| DMF | N,N-Dimethylformamide |
| DMSO | Dimethylsulfoxide |
| NEM | N-Ethylmorpholine |
| rt | room temperature |
| THF | Tetrahydrofuran |
| TOTU | O-[(Cyano(ethoxycarbonyl)methyliden)amino]-1,1,3,3-tetramethyl uronium tetrafluoroborate |
| Z | Benzyl oxycarbonyl |

When in the final step of the synthesis of a compound an acid such as trifluoroacetic acid or acetic acid was used, for example when trifluoroacetic acid was employed to remove a tert-butyl group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt.

Example 1

1-(4-Cyano-phenyl)-3-[-(1-phenyl-ethylamino)-phenyl]-urea 1.16 g (10.8 mmol) 1,2-phenylene diamine was dissolved in 10 ml dimethyl formamide, 2.1 g (15 mmol) potassium carbonate and 1.47 ml (10.8 mmol) 1-bromo-1-phenylethane were added with stirring. After 8 hours (h) at rt, most of the starting materials were consumed. Potassium bromide was filtered off, the solvent removed, the mixture redissolved in 20 ml THF and then 1,15 g (8 mmol) 4-cyanophenylisocyanate were slowly added and stirred for another 50 h at rt. The mixture was worked up by filtration, evaporated to dryness, dissolved in ethyl acetate and washed with diluted HCl, sodium carbonate solution and brine.

| | |
|---|---|
| yield: | 2.8 g (98%) |
| $^1$H-NMR (DMSO-d6, 300 MHz): | 1.32; 1.5; 1.65 (2 d, 3 H, CH$_3$); 4.6 (m, 1 H, CH); 6.4–7.8 (mm, 14 H, ar, NH); 8.4; 9.6 (s, 2 H, ar-NH) |
| MS (M+H): | 357.1 |

Example 2

4-{3-[2-(1-Phenyl-ethylamino)-phenyl]-ureido}-benzamidin

The nitrile from example 1 (1.0 g, 2.8 mmol) was dissolved in 35 ml anhydrous MeOH* HCl (saturated at −20° C.) at rt in a closed vessel for 10 h. The solvent was then removed, and the iminoester was again dissolved in anhydrous MeOH. Ammonium acetate (2.15 g) was added and the mixture stirred for 16 h. After removal of the solvent, adding ethanol and filtration purified the crude product.

| | |
|---|---|
| $^1$H-NMR (DMSO-d6, 300 MHz): | 1.5; 1.8 (2 d, 3 H, CH$_3$); 4.6 (2 m, 1 H, CH); 5.7–7.8 (mm, ar, NH) |
| MS (M+H): | 375.2 |

Example 3

4-[3-(2-{1-[4-carboxyphenyl]-ethylamino}-phenyl)-ureido]-benzonitrile 12.8 g (88.8 mmol) 4-cyanophenylisocyanat were dissolved in 500 ml diethyl ether at rt. 9.6 g (88.8 mmol) o-phenylene diamine were added with stirring. After stirring overnight, the reaction mixture was filtrated and the solid washed with diethylether. The so prepared mono-urea derivative was sufficient pure for further reactions. 3.78 (15 mmol) were dissolved in 30 ml anhydrous dry DMF, 3.44 g (15 mmol) 4-(1-bromoethyl)-benzoic acid and 2 g potassium carbonate were added and stirred for 3 days at rt. The solvent was removed under reduced pressure, the product dissolved in ethyl acetate and extracted with 1 m HCl, water and brine. The organic phase was dried over sodium sulfate and the solvent removed under reduced pressure.

| | |
|---|---|
| yield: | 26 g (73%) |
| 1H-NMR: | ¹H-NMR (DMSO-d6, 300 MHz): 1.32; 1.5; (2 d, 3 H, CH₃); 4.53,; 4.80 (2 m, 1 H, CH); 5.30–8.05 (mm, 14 H, ar, NH); 9.4 (s, 1 H, NH); 12.80 (s, 1 H, COOH) |
| MS (M + H): | 401.22 |

Example 4

4-[3-(2-{1-[4-(Morpholine-4-carbonyl)-phenyl]-ethylamino}-phenyl)-ureido]-benzonitrile The carboxylic acid according to example 3 (94 mg, 0,235 mmol) was dissolved in 4 ml anhydrous and amine free DMF. At rt 85 mg (0,265 mmol) TOTU and 34 μl (0,265 mmol) NEM were added and the mixture was stirred for 30 minutes (min). Then the same amount NEM and morpholine (24 mg, 0,265 mmol) in 1 ml DMF were added. After stirring for 16 h at rt, the solvent was removed and the remainings dissolved in ethyl acetate. Extraction with sodium hydrogen carbonate (twice), water, 1 m HCl, water and brine. The solvent was removed and the residue purified by chromatography.

| | |
|---|---|
| yield: | 84 mg (76%) |
| MS (M + H): | 470.25 |

Example 5

4-[3-(2-{1-[4-(morpholine-4-carbonyl)-phenyl]-ethylamino}-phenyl)-ureido]-benzamidine acetate 47 mg (0,1 mmol) of the cyano-compound of example 4 was dissolved at −20° C. in 10 ml saturated HCl in dry MeOH. After 16 h at rt the solvent was evaporated, remaining HCl removed by codestillation with toluene and the residue redissolved in a 2 m solution of ammonium acetate in dry methanol (4 ml). After 2 days at rt, the solvent was removed; water (2 ml) was added to the remaining mixture of excess ammonium acetate and product and the insoluble product isolated by filtration and dried.

| | |
|---|---|
| yield: | 31 mg (64% of theory) |
| MS (M + H): | 487.32 |

Analogously to the above examples the following example compounds were prepared. The examples in Table 1 show the structures of the prepared compounds.

TABLE 1

| Example | Molstructure | | mol weight (mono- or di-salt included) | MS [M + H] |
|---|---|---|---|---|
| 6 | 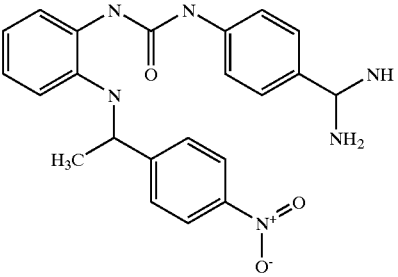 | | 418.459 | 419.32 |
| 7 | 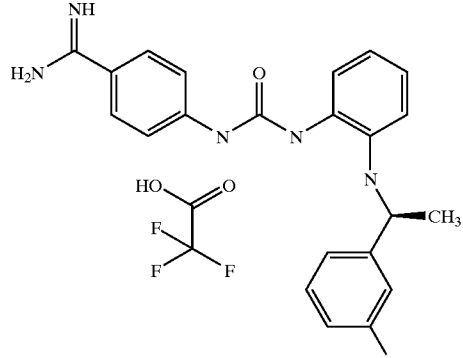 | Chiral | 680.4061 | 454.24 |

TABLE 1-continued

| Example | Molstructure | mol weight (mono- or di-salt included) | MS [M + H] |
|---|---|---|---|
| 8 | Chiral | 680.4061 | 454.24 |
| 9 | | 555.477 | 443.50 |
| 10 | | 556.37 | 443.20 |
| 11 | | 482.965 | 446.10 |

TABLE 1-continued
| Example | Molstructure | | mol weight (mono- or di-salt included) | MS [M + H] |
|---|---|---|---|---|
| 12 | 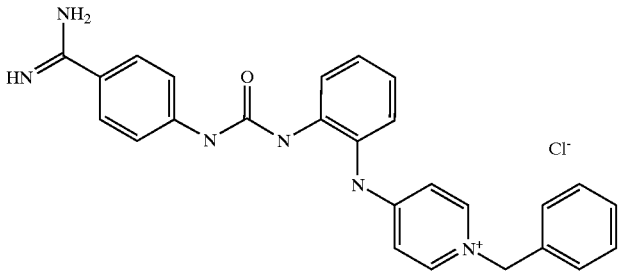 | | 472.978 | 438.20 |
| 13 | 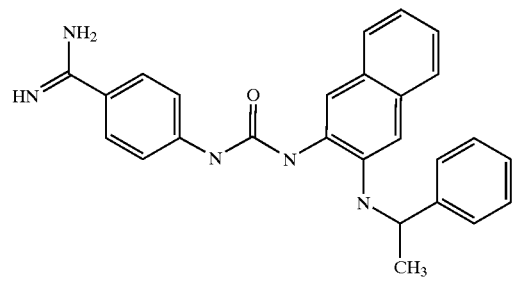 | | 423.517 | 429.00 |
| 14 | 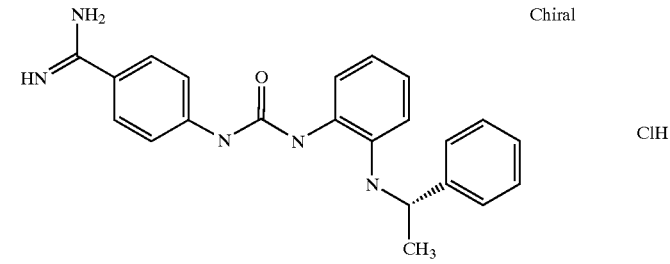 | Chiral | 409.919 | 375.20 |
| 15 | 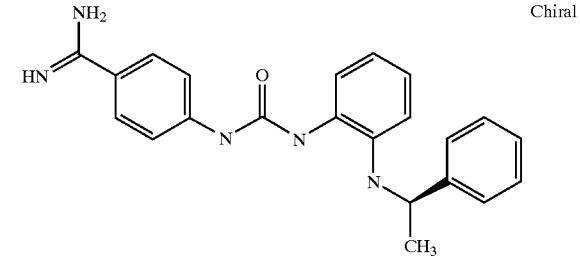 | Chiral | 409.9186 | 375.20 |
| 16 | 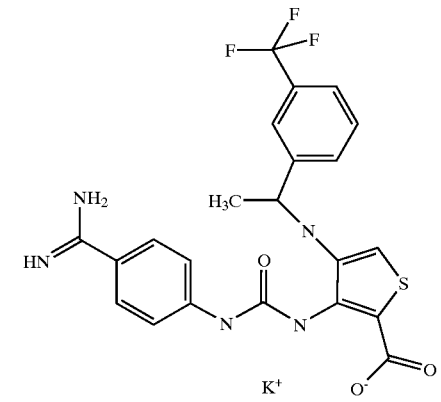 | | 529.5821 | 492.40 |

TABLE 1-continued

| Example | Molstructure | mol weight (mono- or di-salt included) | MS [M + H] |
|---|---|---|---|
| 17 | | 541.9797 | 506.10 |
| 18 | | 491.9425 | 457.30 |
| 19 | | 630.7284 | 572.33 |
| 20 | | 610.6755 | 551.30 |
| 21 | | 610.6755 | 551.39 |

TABLE 1-continued

| Example | Molstructure | mol weight (mono- or di- salt included) | MS [M + H] |
|---|---|---|---|
| 22 | | 658.7638 | 599.38 |
| 23 | | 679.1817 | 619.34 |
| 24 | | 644.7555 | 585.33 |
| 25 | | 668.6538 | 609.36 |

TABLE 1-continued

| Example | Molstructure | mol weight (mono- or di-salt included) | MS [M + H] |
|---|---|---|---|
| 26 | | 608.6596 | 549.36 |
| 27 | | 624.7026 | 565.38 |
| 28 | | 659.7701 | 600.37 |
| 29 | | 616.7013 | 557.30 |
| 30 | | 634.763 | 575.35 |

TABLE 1-continued

| Example | Molstructure | mol weight (mono- or di-salt included) | MS [M + H] |
|---|---|---|---|
| 31 | | 621.62 | 508.25 |
| 32 | | 570.58 | 457.25 |
| 33 | | 674.61 | 561.25 |
| 34 | | 688.64 | 575.30 |
| 35 | | 664.65 | 551.25 |

TABLE 1-continued

| Example | Molstructure | mol weight (mono- or di-salt included) | MS [M + H] |
|---|---|---|---|
| 36 | | 641.05 | 528.30 |
| 37 | | 612.66 | 500.30 |
| 38 | | 664.6468 | 551.25 |
| 39 | | 674.6082 | 561.25 |
| 40 | | 447.5022 | 447.40 |

Pharmacological Testing

The ability of the compounds of the formula I to inhibit factor VIIa or other enzymes like factor Xa, thrombin, plasmin, or trypsin can be assessed by determining the concentration of the compound of the formula I that inhibits enzyme activity by 50%, i.e. the $IC_{50}$ value, which is related to the inhibition constant Ki. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formula I. For calculating the inhibition constant Ki, the $IC_{50}$ value is corrected for competition with substrate using the formula $$Ki=IC_{50}/\{1+(\text{substrate concentration}/Km)\}$$

wherein Km is the Michaelis-Menten constant (Chen and Prusoff, Biochem. Pharmacol. 22 (1973), 3099–3108; I. H. Segal, Enzyme Kinetics, 1975, John Wiley & Sons, New York, 100–125; which are incorporated herein by reference).

a) Factor VIIa (FVIIa) Assay

The inhibitory activity (expressed as inhibition constant Ki(FVIIa)) of the compounds of formula I towards factor VIIa/tissue factor activity was determined using a chromogenic assay essentially as described previously (J. A. Ostrem et al., Biochemistry 37 (1998) 1053–1059 which is incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 μl human factor VIIa and TF (5 nM and 10 nM, respective final concentration) combined with 40 μl of inhibitor dilutions in 10% DMSO/TBS-PEG buffer (50 mM Tris, 15 mM NaCl, 5 mM $CaCl_2$, 0.05% PEG 8000, pH 8.15). Following a 15 minute preincubation period, the assay was initiated by the addition of 35 μl of the chromogenic substrate S-2288 (D-Ile-Pro-Arg-p-nitroanilide, Pharmacia Hepar Inc., 500 μM final concentration).

The following test results (inhibition constants Ki(FVIIa)) were obtained:

| Example Compound | Ki (FVIIa) [nM] |
|---|---|
| 2 | 700 |
| 5 | 188 |
| 15 | 103 |
| 18 | 44400 |
| 19 | 51 |
| 24 | 98 |
| 30 | 282 |
| 37 | 56 |
| 39 | 935 |

What is claimed is:

1. A compound of the formula I,

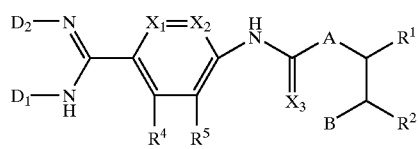

wherein:

$D_1$ and $D_2$ independently from one another are a hydrogen atom, —C(O)—$(C_1$-$C_6)$-alkyl, —C(O)-aryl, —C(O)—$(C_1$-$C_6)$-alkyl-aryl, —C(O)—O—$(C_1$-$C_6)$-alkyl, —C(O)—O—$(C_1$-$C_6)$-alkyl-aryl, —C(O)—O—$(C_1$-$C_6)$-aryl or —$NH_2$; or $D_1$ is a hydrogen atom, when $D_2$ is —OH, —O—C(O)—$(C_1$-$C_6)$-alkyl, —O—C(O)-aryl, —O—C(O)—$(C_1$-$C_6)$-alkyl-aryl or —$NH_2$; or $D_2$ is a hydrogen atom, when $D_1$ is —OH, —O—C(O)—$(C_1$-$C_6)$-alkyl, —O—C(O)-aryl, —O—C(O)—$(C_1$-$C_6)$-alkyl-aryl or —$NH_2$; or $D_1$ and $D_2$ together with the nitrogen atom to which they are attached form a cycle of the formula VIII

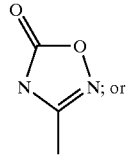

$D_1$ and $R^4$ or $D_2$ and $R^4$ together form a cycle of the formulae VIIIa to VIIId,

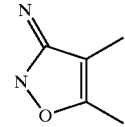

VIIIa

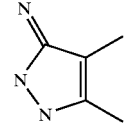

VIIIb

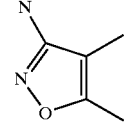

VIIIc

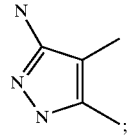

VIIId $X_1$ and $X_2$, independently from one another, are a nitrogen atom, or a carbon atom substituted by $R^{4a}$, wherein $R^{4a}$ is a hydrogen atom, —$(C_1$-$C_6)$-alkyl, —OH, —O—$(C_1$-$C_6)$-alkyl, halogen, —$NH_2$ or —$NO_2$;

$R^4$ and $R^5$ independently from one another are a hydrogen atom, —$(C_1$-$C_6)$-alkyl, —OH, —O—$(C_1$-$C_6)$-alkyl, halogen, —$NH_2$ or —$NO_2$;

$X_3$ is an oxygen atom, sulfur atom or NH;

A is —$X_4$—, —N($R^3$)—$X_4$—, or —O—$X_4$— wherein —$X_4$— is a covalent bond, —$CH_2$—, —CH(OH)—, —CH($NH_2$)—, —CH(COOH)—, —CH($CONH_2$)—, —CH($CH_2$—OH)—, —CH(—$CH_2$—$NH_2$)—, —CH(—$CH_2$—COOH)— or —CH(—$CH_2$—$CONH_2$)—, and wherein $R^3$ is a hydrogen atom, —OH or —$NH_2$;

$R^1$ and $R^2$ together with each of the carbon atoms to which they are attached form aryl, wherein aryl is unsubstituted or mono- or disubstituted independently of one another by $R^6$, or form heteroaryl, wherein heteroaryl is unsubstituted or mono- or disubstituted independently of one another by $R^6$, or form a 3- to 8-membered cyclic group, wherein said cyclic group is saturated or partially saturated and unsubstituted or mono- or disubstituted independently of one another by $R^6$ or =O, or form a 3- to 8-membered cyclic group, having up to 1, 2, 3 or 4 heteroatoms chosen from nitrogen, sulfur or oxygen, wherein said cyclic group is saturated or partially saturated and unsubstituted or mono- or disubstituted independently of one another by $R^6$ or =O, wherein $R^6$ is halogen, —$(CH_2)_n$—OH, wherein n is the integer zero, 1 or 2, —$(CH_2)_n$—O—$R^{10}$, wherein $R^{10}$ is —$(C_1$–$C_6)$-alkyl or —$(C_1$–$C_6)$-alkyl-aryl, and n is the integer zero, 1 or 2, —$(CH_2)_n$—$COOR^{11}$, wherein $R^{11}$ is a hydrogen atom, —$(C_1$–$C_6)$-alkyl or —$(C_1$–$C_6)$-alkyl-aryl, and n is the integer zero, 1 or 2, —$(CH_2)_n$—$C(O)N(H)R^{12}$, wherein $R^{12}$ is a hydrogen atom or —$(C_1$–$C_6)$-alkyl, and n is the integer zero, 1 or 2,

—$NO_2$,

—$N(H)R^{12a}$, wherein $R^{12a}$ is a hydrogen atom, formyl, acetyl, sulfonylmethyl, amidosulfonyl or —$(C_1$–$C_6)$-alkyl,

—$CF_3$,

—$SO_2$—$R^{13}$, wherein $R^{13}$ is methyl, ethyl or —$NH_2$,

—CN,

—$(C_1$–$C_6)$-alkyl,

—$(C_1$–$C_6)$-alkyl-aryl,

-heteroaryl,

—$(C_1$–$C_6)$-alkyl-heteroaryl, or

-heterocycloalkyl;

B is

—$N(R^7)$—$(CH$—$(R^8))_p$-aryl, wherein aryl is unsubstituted or mono-, di- or trisubstituted independently of one another by an aryl group substituent selected from the group consisting of 1) —$(C_1$–$C_6)$-alkyl, wherein alkyl is unsubstituted or mono-, di- or trisubstituted independently of one another by =O, =S, —O—$R^{10}$, halogen, aryl or heteroaryl, 2) —$(C_3$–$C_6)$-cycloalkyl, wherein cycloalkyl is unsubstituted or mono-, di- or trisubstituted independently of one another by =O, =S, —O—$R^{10}$, halogen, aryl or heteroaryl,

3) —$CF_3$,

4) —CN,

5) —$NO_2$, 6) halogen,

7) —C(O)—O—$R^{14}$, wherein $R^{14}$ is hydrogen atom or as $R^6$,

8) —C(O)—$(C_0$–$C_6)$-alkyl, wherein alkyl is unsubstituted or mono-, di- or trisubstituted independently of one another by $R^6$, 9) —O—$(C_1$–$C_6)$-alkyl, wherein alkyl is unsubstituted or mono-, di- or trisubstituted independently of one another by $R^6$, 10) —O—$(C_1$–$C_6)$-alkyl-aryl, wherein alkyl and aryl independently of one another are unsubstituted or mono-, di- or trisubstituted independently of one another by $R^6$, 11) —O—$(C_1$–$C_6)$-alkyl-heteroaryl, wherein alkyl and heteroaryl independently of one another are unsubstituted or mono-, di- or trisubstituted independently of one another by $R^6$, 12) —O—C(O)—S—$(C_1$–$C_6)$-alkyl, 13) —O—C(O)—$(C_1$–$C_6)$-alkyl-aryl, wherein alkyl and aryl independently of one another are unsubstituted or mono-, di- or trisubstituted independently of one another by $R^6$, 14) —O—C(O)—$(C_1$–$C_6)$-alkyl, wherein alkyl is unsubstituted or mono-, di- or trisubstituted independently of one another by $R^6$, 15) —O—C(O)—$(C_1$–$C_6)$-alkyl-heteroaryl, wherein alkyl and heteroaryl independently of one another are unsubstituted or mono-, di- or trisubstituted independently of one another by $R^6$, 16) —O—C(O)-aryl, wherein aryl is unsubstituted or mono-, di- or trisubstituted independently of one another by $R^6$, 17) —O—C(O)-heteroaryl, wherein heteroaryl is unsubstituted or mono-, di- or trisubstituted independently of one another by $R^6$, 18) —O—C(O)—NH—$(C_1$–$C_6)$-alkyl-aryl, wherein alkyl and aryl independently of one another are unsubstituted or mono-, di- or trisubstituted independently of one another by $R^6$, 19) —O—C(O)—NH—$(C_1$–$C_6)$-alkyl, wherein alkyl is unsubstituted or mono-, di- or trisubstituted independently of one another by $R^6$, 20) —O—C(O)—NH—$(C_1$–$C_6)$-alkyl-heteroaryl, wherein alkyl and heteroaryl independently of one another are unsubstituted or mono-, di- or trisubstituted independently of one another by $R^6$, 21) —O—C(O)—NH-aryl, wherein aryl is unsubstituted or mono-, di- or trisubstituted independently of one another by $R^6$, 22) —O—C(O)—NH-heteroaryl, wherein heteroaryl is unsubstituted or mono-, di- or trisubstituted independently of one another by $R^6$, 23) aryl, wherein aryl is unsubstituted or mono-, di- or trisubstituted independently of one another by $R^6$, 24) —O-aryl, wherein —O-aryl is unsubstituted or mono-, di- or trisubstituted independently of one another by $R^6$, 25) heteroaryl, wherein heteroaryl is unsubstituted or mono-, di- or trisubstituted independently of one another by $R^6$, 26) —O-heteroaryl, wherein —O-heteroaryl is unsubstituted or mono-, di- or trisubstituted independently of one another by $R^6$, 27) —$(CH_2)_r$—$S(O)_s$—$R^{15}$, wherein —$R^{15}$ is a) —OH, provided that s is only 2, b) —$(C_1$–$C_6)$-alkyl, wherein alkyl is unsubstituted or mono-, di- or trisubstituted independently of one another by $R^6$, c) aryl, wherein aryl is unsubstituted or mono-, di- or trisubstituted independently of one another by $R^6$, d) —$(C_1$–$C_6)$-alkyl-aryl, wherein alkyl and aryl independently of one another are unsubstituted or mono-, di- or trisubstituted independently of one another by $R^6$, or e) —$N(R^{16})_2$, wherein $R^{16}$ independently of one another are a hydrogen atom or $R^{15}$ a) to $R^{15}$ d), provided that s is only 2, r is the integer zero, 1, 2, or 3, and s is the integer zero, 1 or 2, 28) —$N(R^{17})_2$, wherein $R^{17}$ independently of one another are a) a hydrogen atom, b) —($C_1$–$C_6$)-alkyl, wherein alkyl is unsubstituted or mono-, di- or trisubstituted independently of one another by an aryl group substituent selected from the group consisting of aryl group substituents 1) to 27),
c) aryl, wherein aryl is unsubstituted or mono-, di- or trisubstituted independently of one another by an aryl group substituent selected from the group consisting of aryl group substituents 1) to 27) or two adjacent carbon atoms of the aryl residue form a dioxolan residue,
d) —($C_1$–$C_6$)-alkyl-aryl, wherein alkyl and aryl independently of one another are unsubstituted or mono-, di- or trisubstituted independently of one another by an aryl group substituent selected from the group consisting of aryl group substituents 1) to 27) or two adjacent carbon atoms of the aryl residue form a dioxolan residue,
e) heteroaryl, wherein heteroaryl is unsubstituted or mono-, di- or trisubstituted independently of one another by an aryl group substituent selected from the group consisting of aryl group substituents 1) to 27) or ═O,
f) —($C_1$–$C_6$)-alkyl-heteroaryl, wherein alkyl and heteroaryl independently of one another are unsubstituted or mono-, di- or trisubstituted independently of one another by an aryl group substituent selected from the group consisting of aryl group substituents 1) to 27) or ═O,
g) —C(O)—$R^{18}$, wherein $R^{18}$ is
  1) a hydrogen atom,
  2) —($C_1$–$C_6$)-alkyl, wherein alkyl is unsubstituted or mono-, di- or trisubstituted independently of one another by $R^6$,
  3) aryl, wherein aryl is unsubstituted or mono-, di- or trisubstituted independently of one another by $R^6$,
  4) —($C_1$–$C_6$)-alkyl-aryl, wherein alkyl and aryl independently of one another are unsubstituted or mono-, di- or trisubstituted by $R^6$, or
  5) heteroaryl, wherein heteroaryl is unsubstituted or mono-, di- or trisubstituted independently of one another by $R^6$, or
  6) —($C_1$–$C_6$)-alkyl-heteroaryl, wherein alkyl and heteroaryl independently of one another are unsubstituted or mono-, di- or trisubstituted by $R^6$,
h) —C(S)—$R^{18}$,
i) —C(O)—O—$R^{18}$,
j) —C(O)—N($R^{18}$)$_2$, wherein $R^{18}$ are independent of one another,
k) —S(O)—$R^{18}$,
l) —S(O)$_2$—$R^{18}$,
m) —S(O)—N($R^{18}$)$_2$, wherein $R^{18}$ are independent of one another,
n) —S(O)$_2$—N($R^{18}$)$_2$, wherein $R^{18}$ are independent of one another,
o) —($C_3$–$C_6$)-cycloalkyl, or
p) both $R^{17}$ residues form, together with the nitrogen atom to which they each are bonded, a 3- to 8-membered cyclic group, containing up to 1, 2, 3 or 4 heteroatoms chosen from nitrogen, sulfur or oxygen, wherein said cyclic group is saturated or partially saturated, and wherein said cyclic group is unsubstituted or mono-, di- or trisubstituted independently of one another by $R^6$, and
(29) —C(O)—N($R^{17}$)$_2$, wherein $R^{17}$ are independent of one another.

or B is —N($R^{17}$)$_2$, wherein $R^{17}$ are independent of one another, provided that if there is a single bond between A and B, then A and B are in a cis-conformation to each other;
p is the integer zero, 1 or 2;
$R^7$ is a hydrogen atom, —($C_1$–$C_6$)-alkyl or —OH;
$R^8$ is
  a) a hydrogen atom,
  b) —($C_1$–$C_6$)-alkyl, wherein alkyl is unsubstituted or mono- to totally substituted by fluorine,
  c) —($C_2$–$C_6$)-alkenyl, wherein alkenyl is unsubstituted or mono- di- or trisubstituted by fluorine,
  d) —($C_2$–$C_6$)-alkinyl, wherein alkinyl is unsubstituted or mono- di- or trisubstituted by fluorine,
  e) —($C_0$–$C_3$)-alkyl-($C_3$–$C_6$)-cycloalkyl, wherein alkyl is unsubstituted or mono- to totally substituted by fluorine,
  f) —CN,
  g) aryl, wherein aryl is unsubstituted or mono- or di-substituted by an aryl group substituent selected from the group consisting of aryl group substituents 1) to 28),
  h) heteroaryl, wherein heteroaryl is unsubstituted, mono- or di-substituted by an aryl group substituent selected from the group consisting of aryl group substituents 1) to 28), or
  i) —($C_0$–$C_2$)-alkyl-O—($C_1$–$C_6$)-alkyl,
or B is —O—(CH—($R^8$))$_p$-aryl,
or B is —N($R^7$)—(CH—($R^8$))$_p$-heteroaryl, wherein heteroaryl is unsubstituted or mono- or di-substituted by an aryl group substituent selected from the group consisting of aryl group substituents 1) to 28), or
or B is —S—(CH—($R^8$))$_p$-aryl, wherein aryl is unsubstituted or mono- or di-substituted by an aryl group substituent selected from the group consisting of aryl group substituents 1) to 28); or
a stereoisomeric form, or mixture of stereoisomeric forms thereof, or a physiologically tolerable salt of such compound, stereoisomeric form or mixture.

2. A compound according to claim 1, wherein
$D_1$ and $D_2$ are each a hydrogen atom, or
$D_1$ is a hydrogen atom and $D_2$ is —OH, or
$D_1$ is —OH and $D_2$ is hydrogen atom;
$X_1$ and $X_2$ are independently from one another a —CH— residue or a nitrogen atom;
$R^4$ and $R^5$ independently from one another are a hydrogen atom or halogen;
$X_3$ is an oxygen atom;
A is —NH— or —NH—$CH_2$—;
$R^1$ and $R^2$ together with each carbon atoms to which they are attached form
phenyl, which is unsubstituted or substituted by halogen, —$CF_3$, —($CH_2$)—OH, —($CH_2$)—C(O)—O—$CH_3$, or —($CH_2$)—COOH, or form
thiophenyl, which is unsubstituted or substituted by —($CH_2$)—OH or —($CH_2$)—COOH, or form
naphthyl, which is unsubstituted or substituted by —($CH_2$)—OH or —($CH_2$)—COOH;
B is
—N($R^7$)—(CH—($R^8$))$_p$-aryl, wherein aryl is indanyl, phenyl, tetralinyl or naphthalinyl, each of which may be unsubstituted or mono- or di-substituted independently of one another by
—C(O)—N($R^{17}$)$_2$, wherein $R^{17}$ independently of one another are a) a hydrogen atom,
b) phenyl, wherein phenyl is unsubstituted or mono-, di- or trisubstituted independently of one another by a phenyl group substituent selected from the list consisting of
   1a) —($C_1$–$C_6$)-alkyl, wherein alkyl is unsubstituted or mono-, di- or trisubstituted independently of one another by halogen,
   2a) Cl, F or I,
   3a) —C(O)—O—$R^{14}$, wherein $R^{14}$ is a hydrogen atom or methyl or ethyl,
   4a) —O—($C_1$–$C_3$)-alkyl, wherein each alkyl residue is unsubstituted or mono-, di- or trisubstituted independently of one another by Cl, F or I,
   5a) —O—($C_1$–$C_3$)-alkyl-phenyl, wherein phenyl and alkyl independently of one another are unsubstituted or mono-, di- or trisubstituted independently of one another by Cl, F or I,
   6a) phenyl, wherein phenyl is unsubstituted or mono-, di- or trisubstituted independently of one another by Cl, F or I,
   7a) —O-phenyl, wherein phenyl is unsubstituted or mono-, di- or trisubstituted independently of one another by Cl, F or I, and
   8a) —($CH_2$)$_r$—S(O)$_s$—$R^{15}$, wherein —$R^{15}$ is
      a) methyl or ethyl, or
      b) N($R^{16}$)$_2$, wherein $R^{16}$ is methyl or ethyl, and
   r is the integer zero or 1, and
   s is the integer 1 or 2, or
   two adjacent carbon atoms of the phenyl residue form a dioxolan residue,
c) —($C_1$–$C_6$)-alkyl-phenyl, wherein alkyl and phenyl independently of one another are unsubstituted or mono-, di- or trisubstituted independently of one another by a phenyl group substituent selected from the list consisting of phenyl group substituents 1a) to 8a), or
   two adjacent carbon atoms of the phenyl residue form a dioxolan residue,
d) heteroaryl, wherein heteroaryl is selected from the group consisting of imidazolyl, benzimidazolyl, morpholinyl, oxazolyl, benzoxazolyl, isobenzofuran, thiazolyl, thiophenyl, indazolyl, benzothiazolyl, indolyl, indolinyl, and pyridinyl and wherein heteroaryl is unsubstituted or mono-, di- or trisubstituted independently of one another by phenyl or by a phenyl group substituent selected from the list consisting of phenyl group substituents 1a) to 8a), or by =O,
e) —($C_1$–$C_6$)-alkyl-heteroaryl, wherein heteroaryl is selected from the group consisting of imidazolyl, isobenzofuranyl, benzimidazolyl, morpholinyl, oxazolyl, benzoxazolyl, thiazolyl, thiophenyl, indazolyl, benzothiazolyl, indolyl, indolinyl, and pyridinyl, and wherein alkyl and heteroaryl independently of one another are unsubstituted or mono-, di- or trisubstituted independently of one another by phenyl by a phenyl group substituent selected from the list consisting of phenyl group substituents 1a) to 8a), or by =O,
f) both $R^{17}$ residues form, together with the nitrogen atom to which they each are bonded, a 3- to 8-membered cyclic group selected from the group consisting of morpholinyl, indazolyl, indolyl, indolinyl, aziridinyl, pyrazolyl, pyrazinolyl, pyrrolidinyl, pyrrolinyl, piperidinyl, piperazinyl, imidazolinyl, imidazolidinyl, thiomorpholinyl, pyridazinolidinyl, pyridazinolinyl and isoindolyl and wherein said cyclic group is unsubstituted or mono-, di- or trisubstituted independently of one another by phenyl or by a phenyl group substituent selected from the list consisting of phenyl group substituents 1a) to 8a), or by =O, or $R^{17}$ is
h) —($C_3$–$C_6$)-cycloalkyl,
or when B is —N($R^7$)—(CH—($R^8$))$_p$-aryl, wherein aryl is indanyl, phenyl, tetralinyl or naphthalinyl, aryl may be unsubstituted or mono- or di-substituted independently of one another by an aryl group substituent selected from the list further consisting of Cl, F, Br, —$CF_3$, —$NO_2$, phenyl, phenyloxy, benzyloxy, methyl, methoxy, carboxyl, carboxylalkyl or carboxylalkylphenyl;,
p is the integer zero or 1,
$R^7$ is a hydrogen atom,
$R^8$ is a hydrogen atom, —($C_1$–$C_2$)-alkyl which may be unsubstituted or all hydrogen atoms are replaced by fluorine, or $R^8$ is —CN, phenyl wherein phenyl is unsubstituted or mono- or di-substituted by methoxy or halogen, or $R^8$ is —($C_0$–$C_2$)-alkyl-O—($C_1$–$C_4$)-alkyl, cyclopropylmethyl, or ethinyl;
or B is —O—(CH—($R^8$))$_p$-phenyl, where $R^8$ is a hydrogen atom, —($C_1$–$C_2$)-alkyl which may be unsubstituted or all hydrogen atoms are replaced by fluorine, or $R^8$ is —CN, phenyl wherein phenyl is unsubstituted or mono- or di-substituted by methoxy or halogen, or $R^8$ is —($C_0$–$C_2$)-alkyl-O—($C_1$–$C_4$)-alkyl, cyclopropylmethyl, or ethinyl;
or B is —N($R^{17}$)$_2$, wherein $R^{17}$ independently of one another are a hydrogen atom or heteroaryl residue selected from the group consisting of aziridine, oxirane, azetidine, pyrrole, furan, thiophene, dioxole, imidazole, pyrazole, oxazole, isoxazole, thiazole, isothiazole, thiadiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, isobenzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines and pyridopyrimidines, each of which heteroaryl groups may be unsubstituted or mono substituted by Br, Cl, F, —$CF_3$, =O, —$NO_2$, phenyl, phenoxy, methyl, benzyl, benzyloxy, methyl, methoxy, carboxy, carboxyalkyl or carboxyalkylaryl.

3. A compound according to claim 1 or claim 2, wherein
$D_1$ and $D_2$ are each a hydrogen atom;
$X_1$ and $X_2$ are each a —CH— residue;
$R^4$ and $R^5$ are each a hydrogen atom;
$X_3$ is an oxygen atom;
A is —NH— or —NH—$CH_2$—;
$R^1$ and $R^2$ together with each of the carbon atoms to which they are attached form phenyl, which is unsubstituted or substituted by halogen, —$CF_3$ or —($CH_2$)—C(O)—O—$CH_3$, or
$R^1$ and $R^2$ together with each of the carbon atoms to which they are attached form thiophene, substituted by —($CH_2$)—C(O)—O—$CH_3$ or —($CH_2$)—COOH, or R$^1$ and R$^2$ together with each of the carbon atoms to which they are attached form naphthyl;

B is —N(R$^7$)—(CH—(R$^8$))$_p$-phenyl,
  wherein phenyl is unsubstituted or mono- or di-substituted independently of one another by —C(O)—N(R$^{17}$)$_2$, wherein R$^{17}$ independently of one another are
  a) a hydrogen atom,
  b) phenyl, wherein phenyl is unsubstituted or monosubstituted by
    —(CH$_2$)$_r$—S(O)$_s$—R$^{15}$, wherein —R$^{15}$ is methyl or R$^{15}$ is —N(R$^{16}$)$_2$, wherein R$^{16}$ methyl, and r is the integer zero or 1, and s is the integer 1 or 2,
  c) —(C$_1$-C$_2$)-alkyl-phenyl, wherein phenyl is unsubstituted or mono- by
    —(CH$_2$)$_r$—S(O)$_s$—R$^{15}$, wherein —R$^{15}$ is methyl or R$^{15}$ is —N(R$^{16}$)$_2$, wherein R$^{16}$ methyl, and r is the integer zero or 1, and s is the integer 1 or 2,
  d) heteroaryl, wherein heteroaryl is benzoxazolyl, morpholinyl, isobenzofuranyl, thiophenyl or pyridinyl and is unsubstituted or monosubstituted by phenyl or =O, or
  e) —(C$_3$-C$_6$)-cycloalkyl,
  p is the integer zero or 1,
  R$^7$ is a hydrogen atom, and
  R$^8$ is hydrogen atom or methyl, or B is
  —N(R$^{17}$)$_2$, wherein R$^{17}$ independently of one another are a hydrogen atom or pyridinyl, which is unsubstituted or mono substituted by benzyl.

4. A pharmaceutical preparation, comprising a compound according to claim 1 and a pharmaceutically acceptable carrier.

5. A method of inhibiting factor VIIa, in a patient in need thereof, comprising administering to said patient a pharmaceutically effective amount of a compound according to claim 1.

6. A method of inhibiting blood clotting, in a patient in need thereof, comprising administering to said patient a pharmaceutically effective amount of a compound according to claim 1.

7. A method of inhibiting an inflammatory response, in a patient in need thereof, comprising administering to said patient a pharmaceutically effective amount of a compound according to claim 1.

8. A method of treating a cardiovascular disorder, in a patient in need thereof, comprising administering to said patient a pharmaceutically effective amount of a compound according to claim 1.

9. A method of treating a thromboembolic disease, in a patient in need thereof, comprising administering to said patient a pharmaceutically effective amount of a compound according to claim 1.

10. A method of treating restenosis, in a patient in need thereof, comprising administering to said patient a pharmaceutically effective amount of a compound according to claim 1.

11. A compound of the formula I,

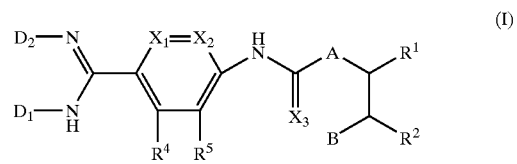

(I)

wherein:
  D$_1$ and D$_2$ independently from one another are a hydrogen atom, —C(O)—(C$_1$-C$_6$)-alkyl, —C(O)-aryl, —C(O)—(C$_1$-C$_6$)-alkyl-aryl, —C(O)—O—(C$_1$-C$_6$)-alkyl, —C(O)—O—(C$_1$-C$_6$)-alkyl-aryl, —C(O)—O—(C$_1$-C$_6$)-aryl or —NH$_2$; or
  D$_1$ is a hydrogen atom, when D$_2$ is —OH, —O—C(O)—(C$_1$-C$_6$)-alkyl, —O—C(O)-aryl, —O—C(O)—(C$_1$-C$_5$)-alkyl-aryl or —NH$_2$; or
  D$_2$ is a hydrogen atom, when D$_1$ is —OH, —O—C(O)—(C$_1$-C$_6$)-alkyl, —O—C(O)-aryl, —O—C(O)—(C$_1$-C$_6$)-alkyl-aryl or —NH$_2$; or
  D$_1$ and D$_2$ together with the nitrogen atom to which they are attached form a cycle of the formula VIII

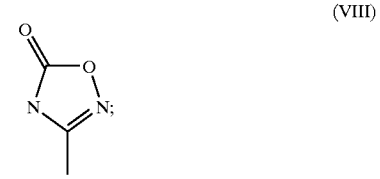

(VIII)

X$_1$ and X$_2$ are each a carbon atom substituted by R$^{4a}$, wherein R$^{4a}$ is a hydrogen atom, —(C$_1$-C$_6$)-alkyl, —OH, —O—(C$_1$-C$_6$)-alkyl, halogen, —NH$_2$ or —NO$_2$;

R$^4$ and R$^5$ independently from one another are a hydrogen atom, —(C$_1$-C$_6$)-alkyl, —OH, —O—(C$_1$-C$_6$)-alkyl, halogen, —NH$_2$ or —NO$_2$;

X$_3$ is an oxygen atom, sulfur atom or NH;

A is —X$_4$—, —N(R$^3$)—X$_4$—, or —O—X$_4$— wherein —X$_4$— is —CH$_2$—, —CH(OH)—, —CH(NH$_2$)—, —CH(COOH)—, —CH(CONH$_2$)—, —CH(CH$_2$—OH)—, —CH(—CH$_2$—NH$_2$)—, —CH(—CH$_2$—COOH)— or —CH(—CH$_2$—CONH$_2$)—, and wherein R$^3$ is a hydrogen atom, —OH or —NH$_2$;

R$^1$ and R$^2$ together with each of the carbon atoms to which they are attached form
  phenyl, wherein phenyl is unsubstituted or mono or disubstituted independently of one another by R$^6$,
  wherein R$^6$ is
    halogen,
    —(CH$_2$)$_n$—OH, wherein n is the integer zero, 1 or 2,
    —(CH$_2$)$_n$—O—R$^{10}$, wherein R$^{10}$ is —(C$_1$-C$_6$)-alkyl or —(C$_1$-C$_6$)-alkyl-aryl, and n is the integer zero, 1 or 2,
    —(CH$_2$)$_n$—COOR$^{11}$, wherein R$^{11}$ is a hydrogen atom, —(C$_1$-C$_6$)-alkyl or —(C$_1$-C$_6$)-alkyl-aryl, and n is the integer zero, 1 or 2,
    —(CH$_2$)$_n$—C(O)N(H)R$^{12}$, wherein R$^{12}$ is a hydrogen atom or
    —(C$_1$-C$_6$)-alkyl, and n is the integer zero, 1 or 2,
    —NO$_2$,
    N(H)R$^{12a}$, wherein R$^{12a}$ is a hydrogen atom, formyl, acetyl, sulfonylmethyl, amidosulfonyl or —(C$_1$-C$_6$)-alkyl, —$CF_3$,
—$SO_2$—$R^{13}$, wherein $R^{13}$ is methyl, ethyl or —$NH_2$,
—CN,
—$(C_1-C_6)$-alkyl,
—$(C_1-C_6)$-alkyl-aryl,
-heteroaryl,
—$(C_1-C_6)$-alkyl-heteroaryl, or
-heterocycloalkyl;

B is

—$N(R^7)$—$(CH$—$(R^8))_p$-aryl, wherein aryl is unsubstituted or mono-, di- or trisubstituted independently of one another by an aryl group substituent selected from the group consisting of
1) —$(C_1-C_6)$-alkyl, wherein alkyl is unsubstituted or mono-, di- or trisubstituted independently of one another by =O, =S, —O—$R^{10}$, halogen, aryl or heteroaryl,
2) —$(C_3-C_6)$-cycloalkyl, wherein cycloalkyl is unsubstituted or mono-, di- or trisubstituted independently of one another by =O, =S, —O—$R^{10}$, halogen, aryl or heteroaryl,
3) —$CF_3$,
4) —CN,
5) —$NO_2$,
6) halogen,
7) —C(O)—O—$R^{14}$, wherein $R^{14}$ is hydrogen atom or as $R^6$,
8) —C(O)—$(C_0-C_6)$-alkyl, wherein alkyl is unsubstituted or mono-, di- or trisubstituted independently of one another by $R^6$,
9) —O—$(C_1-C_6)$-alkyl, wherein alkyl is unsubstituted or mono-, di- or trisubstituted independently of one another by $R^6$,
10) —O—$(C_1-C_6)$-alkyl-aryl, wherein alkyl and aryl independently of one another are unsubstituted or mono-, di- or trisubstituted independently of one another by $R^6$,
11) —O—$(C_1-C_6)$-alkyl-heteroaryl, wherein alkyl and heteroaryl independently of one another are unsubstituted or mono-, di- or trisubstituted independently of one another by $R^6$,
12) —O—C(O)—S—$(C_1-C_6)$-alkyl,
13) —O—C(O)—$(C_1-C_6)$-alkyl-aryl, wherein alkyl and aryl independently of one another are unsubstituted or mono-, di- or trisubstituted independently of one another by $R^6$,
14) —O—C(O)—$(C_1-C_6)$-alkyl, wherein alkyl is unsubstituted or mono-, di- or trisubstituted independently of one another by $R^6$,
15) —O—C(O)—$(C_1-C_6)$-alkyl-heteroaryl, wherein alkyl and heteroaryl independently of one another are unsubstituted or mono-, di- or trisubstituted independently of one another by $R^6$,
16) —O—C(O)-aryl, wherein aryl is unsubstituted or mono-, di- or trisubstituted independently of one another by $R^6$,
17) —O—C(O)-heteroaryl, wherein heteroaryl is unsubstituted or mono-, di- or trisubstituted independently of one another by $R^6$,
18) —O—C(O)—NH—$(C_1-C_6)$-alkyl-aryl, wherein alkyl and aryl independently of one another are unsubstituted or mono-, di- or trisubstituted independently of one another by $R^6$,
19) —O—C(O)—NH—$(C_1-C_6)$-alkyl, wherein alkyl is unsubstituted or mono-, di- or trisubstituted independently of one another by $R^6$,
20) —O—C(O)—NH—$(C_1-C_6)$-alkyl-heteroaryl, wherein alkyl and heteroaryl independently of one another are unsubstituted or mono-, di- or trisubstituted independently of one another by $R^6$,
21) —O—C(O)—NH-aryl, wherein aryl is unsubstituted or mono-, di- or trisubstituted independently of one another by $R^6$,
22) —O—C(O)—NH-heteroaryl, wherein heteroaryl is unsubstituted or mono-, di- or trisubstituted independently of one another by $R^6$,
23) aryl, wherein aryl is unsubstituted or mono-, di- or trisubstituted independently of one another by $R^6$,
24) —O-aryl, wherein —O-aryl is unsubstituted or mono-, di- or trisubstituted independently of one another by $R^6$,
25) heteroaryl, wherein heteroaryl is unsubstituted or mono-, di- or trisubstituted independently of one another by $R^6$,
26) —O-heteroaryl, wherein —O-heteroaryl is unsubstituted or mono-, di- or trisubstituted independently of one another by $R^6$,
27) —$(CH_2)_r$—$S(O)_s$—$R^{15}$, wherein —$R^{15}$ is
a) —OH, provided that s is only 2,
b) —$(C_1-C_6)$-alkyl, wherein alkyl is unsubstituted or mono-, di- or trisubstituted independently of one another by $R^6$,
c) aryl, wherein aryl is unsubstituted or mono-, di- or trisubstituted independently of one another by $R^8$,
d) —$(C_1-C_6)$-alkyl-aryl, wherein alkyl and aryl independently of one another are unsubstituted or mono-, di- or trisubstituted independently of one another by $R^6$, or
e) —$N(R^{16})_2$, wherein $R^{16}$ independently of one another are a hydrogen atom or $R^{15}$ a) to $R^{15}$ d), provided that s is only 2,
r is the integer zero, 1, 2, or 3, and
s is the integer zero, 1 or 2,
28) —$N(R^{17})_2$, wherein $R^{17}$ independently of one another are
a) a hydrogen atom,
b) —$(C_1-C_6)$-alkyl, wherein alkyl is unsubstituted or mono-, di- or trisubstituted independently of one another by an aryl group substitutent selected from the group consisting of aryl group substituents 1) to 27),
c) aryl, wherein aryl is unsubstituted or mono-, di- or trisubstituted independently of one another by an aryl group substitutent selected from the group consisting of aryl group substituents 1) to 27) or two adjacent carbon atoms of the aryl residue form a dioxolan residue,
d) —$(C_1-C_8)$-alkyl-aryl, wherein alkyl and aryl independently of one another are unsubstituted or mono-, di- or trisubstituted independently of one another by an aryl group substitutent selected from the group consisting of aryl group substituents 1) to 27) or two adjacent carbon atoms of the aryl residue form a dioxolan residue,
e) heteroaryl, wherein heteroaryl is unsubstituted or mono-, di- or trisubstituted independently of one another by an aryl group substitutent selected from the group consisting of aryl group substituents 1) to 27) or =O,
f) —$(C_1-C_6)$-alkyl-heteroaryl, wherein alkyl and heteroaryl independently of one another are unsubstituted or mono-, di- or trisubstituted independently of one another by an aryl group substitutent selected from the group consisting of aryl group substituents 1) to 27) or =O, g) —C(O)—$R^{18}$, wherein $R^{18}$ is
1) a hydrogen atom,
2) —($C_1$–$C_6$)-alkyl, wherein alkyl is unsubstituted or mono-, di- or trisubstituted independently of one another by $R^6$,
3) aryl, wherein aryl is unsubstituted or mono-, di- or trisubstituted independently of one another by $R^6$,
4) —($C_1$–$C_6$)-alkyl-aryl, wherein alkyl and aryl independently of one another are unsubstituted or mono-, di- or trisubstituted by $R^6$, or
5) heteroaryl, wherein heteroaryl is unsubstituted or mono-, di- or trisubstituted independently of one another by $R^6$, or
6) —($C_1$–$C_6$)-alkyl-heteroaryl, wherein alkyl and heteroaryl independently of one another are unsubstituted or mono-, di- or trisubstituted by $R^6$,
h) —C(S)—$R^{18}$,
i) —C(O)—O—$R^{18}$,
j) —C(O)—N($R^{18}$)$_2$, wherein $R^{18}$ are independent of one another,
k) —S(O)—$R^{18}$,
l) —S(O)$_2$—$R^{18}$,
m) —S(O)—N($R^{18}$)$_2$, wherein $R^{18}$ are independent of one another,
n) —S(O)$_2$—N($R^{18}$)$_2$, wherein $R^{18}$ are independent of one another,
o) —($C_3$–$C_6$)-cycloalkyl, or
p) both $R^{17}$ residues form, together with the nitrogen atom to which they each are bonded, a 3- to 8-membered cyclic group, containing up to 1, 2, 3 or 4 heteroatoms chosen from nitrogen, sulfur or oxygen, wherein said cyclic group is saturated or partially saturated, and wherein said cyclic group is unsubstituted or mono-, di- or trisubstituted independently of one another by $R^6$, and
(29) —C(O)—N($R^{17}$)$_2$, wherein $R^{17}$ are independent of one another,
or B is —N($R^{17}$)$_2$, wherein $R^{17}$ are independent of one another, provided that if there is a single bond between A and B, then A and B are in a cis-conformation to each other;
p is the integer zero, 1 or 2;
$R^7$ is a hydrogen atom, —($C_1$–$C_6$)-alkyl or —OH;
$R^8$ is
  c) a hydrogen atom,
  d) —($C_1$–$C_6$)-alkyl, wherein alkyl is unsubstituted or mono- to totally substituted by fluorine,
  c) —($C_2$–$C_6$)-alkenyl, wherein alkenyl is unsubstituted or mono- di- or trisubstituted by fluorine,
  d) —($C_2$–$C_6$)-alkinyl, wherein alkinyl is unsubstituted or mono- di- or trisubstituted by fluorine,
  e) —($C_0$–$C_3$)-alkyl-($C_3$–$C_6$)-cycloalkyl, wherein alkyl is unsubstituted or mono- to totally substituted by fluorine,
  f) —CN,
  g) aryl, wherein aryl is unsubstituted or mono- or di-substituted by an aryl group substitutent selected from the group consisting of aryl group substituents 1) to 28),
  h) heteroaryl, wherein heteroaryl is unsubstituted, mono- or di-substituted by an aryl group substitutent selected from the group consisting of aryl group substituents 1) to 28), or
  i) —($C_0$–$C_2$)-alkyl-O—($C_1$–$C_6$)-alkyl,
or B is —O—(CH—($R^8$))$_p$-aryl,
or B is —N($R^7$)—(CH—($R^8$))$_p$-heteroaryl, wherein heteroaryl is unsubstituted or mono- or di-substituted by an aryl group substitutent selected from the group consisting of aryl group substituents 1) to 28), or or B is —S—(CH—($R^8$))$_p$-aryl, wherein aryl is unsubstituted or mono- or di-substituted by an aryl group substitutent selected from the group consisting of aryl group substituents 1) to 28); or
a sterioisomeric form, or mixture of stereoisomeric forms thereof, or a physiologically tolerable salt of such compound, stereoisomeric form or mixture.

12. A compound according to claim 11, wherein
$D_1$ and $D_2$ are each a hydrogen atom, or
$D_1$ is a hydrogen atom and $D_2$ is —OH, or
$D_1$ is —OH and $D_2$ is hydrogen atom;
$X_1$ and $X_2$ are independently from one another a —CH— residue;
$R^4$ and $R^5$ independently from one another are a hydrogen atom or halogen;
$X_3$ is an oxygen atom;
A is —NH— or —NH—$CH_2$—;
$R^1$ and $R^2$ together with each carbon atoms to which they are attached form
phenyl, which is unsubstituted or substituted by halogen, —$CF_3$, —($CH_2$)—OH, —($CH_2$)—C(O)—O—$CH_3$, or —($CH_2$)—COOH;
B is
—N($R^7$)—(CH—($R^8$))$_p$-aryl, wherein aryl is indanyl, phenyl, tetralinyl or naphthalinyl, each of which may be unsubstituted or mono- or di-substituted independently of one another by
—C(O)—N($R^{17}$)$_2$, wherein $R^{17}$ independently of one another are
  a) a hydrogen atom,
  b) phenyl, wherein phenyl is unsubstituted or mono-, di- or trisubstituted independently of one another by a phenyl group substituent selected from the list consisting of
    1a) —($C_1$–$C_6$)-alkyl, wherein alkyl is unsubstituted or mono-, di- or trisubstituted independently of one another by halogen,
    2a) Cl, F or I,
    3a) —C(O)—O—$R^{14}$, wherein $R^{14}$ is a hydrogen atom or methyl or ethyl,
    4a) —O—($C_1$–$C_3$)-alkyl, wherein each alkyl residue is unsubstituted or mono-, di- or trisubstituted independently of one another by Cl, F or I,
    5a) —O—($C_1$–$C_3$)-alkyl-phenyl, wherein phenyl and alkyl independently of one another are unsubstituted or mono-, di- or trisubstituted independently of one another by Cl, F or I,
    6a) phenyl, wherein phenyl is unsubstituted or mono-, di- or trisubstituted independently of one another by Cl, F or I,
    7a) —O-phenyl, wherein phenyl is unsubstituted or mono-, di- or trisubstituted independently of one another by Cl, F or I, and
    8a) —($CH_2$)$_r$—S(O)$_s$—$R^{15}$, wherein —$R^{15}$ is
      a) methyl or ethyl, or
      b) N($R^{16}$)$_2$, wherein $R^{16}$ is methyl or ethyl, and
    r is the integer zero or 1, and
    s is the integer 1 or 2, or
    two adjacent carbon atoms of the phenyl residue form a dioxolan residue,
  c) —($C_1$–$C_6$)-alkyl-phenyl, wherein alkyl and phenyl independently of one another are unsubstituted or mono-, di- or trisubstituted independently of one another by a phenyl group substituent selected from the list consisting of phenyl group substituents 1a) to 8a), or two adjacent carbon atoms of the phenyl residue form a dioxolan residue, d) heteroaryl, wherein heteroaryl is selected from the group consisting of imidazolyl, benzimidazolyl, morpholinyl, oxazolyl, benzoxazolyl, isobenzofuran, thiazolyl, thiophenyl, indazolyl, benzothiazolyl, indolyl, indolinyl, and pyridinyl and wherein heteroaryl is unsubstituted or mono-, di- or trisubstituted independently of one another by phenyl or by a phenyl group substituent selected from the list consisting of phenyl group substituents 1a) to 8a), or by =O, e) —($C_1$–$C_6$)-alkyl-heteroaryl, wherein heteroaryl is selected from the group consisting of imidazolyl, isobenzofuranyl, benzimidazolyl, morpholinyl, oxazolyl, benzoxazolyl, thiazolyl, thiophenyl, indazolyl, benzothiazolyl, indolyl, indolinyl, and pyridinyl, and wherein alkyl and heteroaryl independently of one another are unsubstituted or mono-, di- or trisubstituted independently of one another by phenyl by a phenyl group substituent selected from the list consisting of phenyl group substituents 1a) to 8a), or by =O, f) both $R^{17}$ residues form, together with the nitrogen atom to which they each are bonded, a 3- to 8-membered cyclic group selected from the group consisting of morpholinyl, indazolyl, indolyl, indolinyl, aziridinyl, pyrazolyl, pyrazinolyl, pyrrolidinyl, pyrrolinyl, piperidinyl, piperazinyl, imidazolinyl, imidazolidinyl, thiomorpholinyl, pyridazinolidinyl, pyridazinolinyl and isoindolyl and wherein said cyclic group is unsubstituted or mono-, di- or trisubstituted independently of one another by phenyl or by a phenyl group substituent selected from the list consisting of phenyl group substituents 1a) to 8a), or by =O, or $R^{17}$ is h) —($C_3$–$C_6$)-cycloalkyl, or when B is —N($R^7$)—(CH—($R^8$))$_p$-aryl, wherein aryl is indanyl, phenyl, tetralinyl or naphthalinyl, aryl may be unsubstituted or mono- or di-substituted independently of one another by an aryl group substituent selected from the list further consisting of Cl, F, Br, —$CF_3$, —$NO_2$, phenyl, phenyloxy, benzyloxy, methyl, methoxy, carboxyl, carboxylalkyl or carboxylalkylphenyl;

is the integer zero or 1, $R^7$ is a hydrogen atom, $R^8$ is a hydrogen atom, —($C_1$–$C_2$)-alkyl which may be unsubstituted or all hydrogen atoms are replaced by fluorine, or $R^8$ is —CN, phenyl wherein phenyl is unsubstituted or mono- or di-substituted by methoxy or halogen, or $R^8$ is —($C_0$–$C_2$)-alkyl-O—($C_1$–$C_4$)-alkyl, cyclopropylmethyl, or ethinyl;

or B is —O—(CH—($R^8$))$_p$-phenyl, where $R^8$ is a hydrogen atom, —($C_1$–$C_2$)-alkyl which may be unsubstituted or all hydrogen atoms are replaced by fluorine, or $R^8$ is —CN, phenyl wherein phenyl is unsubstituted or mono- or di-substituted by methoxy or halogen, or $R^8$ is —($C_0$–$C_2$)-alkyl-O—($C_1$–$C_4$)-alkyl, cyclopropylmethyl, or ethinyl;

or B is —N($R^{17}$)$_2$, wherein $R^{17}$ independently of one another are a hydrogen atom or heteroaryl residue selected from the group consiting of aziridine, oxirane, azetidine, pyrrole, furan, thiophene, dioxole, imidazole, pyrazole, oxazole, isoxazole, thiazole, isothiazole, thiadiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, isobenzofuran, benzothiophene, 1,3-benzodioxole, benzo[1,4]dioxine, 4H-benzo[1,4] oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines and pyridopyrimidines, each of which heteroaryl groups may be unsubstituted or mono substituted by Br, Cl, F, —$CF_3$, =O, —$NO_2$, phenyl, phenoxy, methyl, benzyl, benzyloxy, methyl, methoxy, carboxy, carboxyalkyl or carboxyalkylaryl.

13. A compound according to claim 11 or claim 12, wherein $D_1$ and $D_2$ are each a hydrogen atom;

$X_1$ and $X_2$ are each a —CH— residue;

$R^4$ and $R^5$ are each a hydrogen atom;

$X_3$ is an oxygen atom;

A is —NH— or —NH—$CH_2$—;

$R^1$ and $R^2$ together with each of the carbon atoms to which they are attached form phenyl, which is unsubstituted or substituted by halogen, —$CF_3$ or —($CH_2$)—C(O)—O—$CH_3$—;

B is —N($R^7$)—(CH—($R^8$))$_p$-phenyl, wherein phenyl is unsubstituted or mono- or di-substituted independently of one another by —C(O)—N($R^{17}$)$_2$, wherein $R^{17}$ independently of one another are a) a hydrogen atom, b) phenyl, wherein phenyl is unsubstituted or mono-substituted by —($CH_2$)$_r$—S(O)$_s$—$R^{15}$, wherein —$R^{15}$ is methyl or $R^{15}$ is —N($R^{16}$)$_2$, wherein $R^{16}$ methyl, and r is the integer zero or 1, and s is the integer 1 or 2, c) —($C_1$–$C_2$)-alkyl-phenyl, wherein phenyl is unsubstituted or mono- by —($CH_2$)$_r$—S(O)$_s$—$R^{15}$, wherein —$R^{15}$ is methyl or $R^{15}$ is —N($R^{16}$)$_2$, wherein $R^{16}$ methyl, and r is the integer zero or 1, and s is the integer 1 or 2, d) heteroaryl, wherein heteroaryl is benzoxazolyl, morpholinyl, isobenzofuranyl, thiophenyl or pyridinyl and is unsubstituted or monosubstituted by phenyl or =O, or e) —($C_3$–$C_6$)-cycloalkyl, p is the integer zero or 1, $R^7$ is a hydrogen atom, and $R^8$ is hydrogen atom or methyl, or B is —N($R^{17}$)$_2$, wherein $R^{17}$ independently of one another are a hydrogen atom or pyridinyl, which is unsubstituted or mono substituted by benzyl.

14. A pharmaceutical preparation, comprising a compound according to claim 11 and a pharmaceutically acceptable carrier.

15. A method of inhibiting factor VIIa, in a patient in need thereof, comprising administering to said patient a pharmaceutically effective amount of a compound according to claim 11.

16. A method of inhibiting blood clotting, in a patient in need thereof, comprising administering to said patient a pharmaceutically effective amount of a compound according to claim 11.

17. A method of inhibiting an inflammatory response, in a patient in need thereof, comprising administering to said patient a pharmaceutically effective amount of a compound according to claim 11.

18. A method of treating a cardiovascular disorder, in a patient in need thereof, comprising administering to said patient a pharmaceutically effective amount of a compound according to claim 11.

19. A method of treating a thromboembolic disease, in a patient in need thereof, comprising administering to said patient a pharmaceutically effective amount of a compound according to claim 11.

20. A method of treating restenosis, in a patient in need thereof, comprising administering to said patient a pharmaceutically effective amount of a compound according to claim 11.

* * * * *